United States Patent
Sakuma et al.

(10) Patent No.: US 9,624,294 B2
(45) Date of Patent: Apr. 18, 2017

(54) ANTIBODY RECOGNIZING N-DOMAIN OF MIDKINE

(75) Inventors: Sadatosi Sakuma, Kanagawa (JP); Maria Halasz, Sydney (AU); Darren Jones, Avalon (AU)

(73) Assignee: Cellmid Limited, Sydney (AU)

( * ) Notice: Subject to any disclaimer, the term of this patent is extended or adjusted under 35 U.S.C. 154(b) by 285 days.

(21) Appl. No.: 14/004,548

(22) PCT Filed: Mar. 13, 2012

(86) PCT No.: PCT/AU2012/000251
§ 371 (c)(1),
(2), (4) Date: Feb. 17, 2014

(87) PCT Pub. No.: WO2012/122590
PCT Pub. Date: Sep. 20, 2012

(65) Prior Publication Data
US 2014/0170144 A1   Jun. 19, 2014

Related U.S. Application Data

(60) Provisional application No. 61/452,337, filed on Mar. 14, 2011.

(51) Int. Cl.
*A61K 39/395* (2006.01)
*C07K 16/22* (2006.01)
*A61K 39/00* (2006.01)

(52) U.S. Cl.
CPC ........ *C07K 16/22* (2013.01); *A61K 2039/505* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,196,265 A | 4/1980 | Koprowski et al. |
| 4,676,980 A | 6/1987 | Segal et al. |
| 4,816,567 A | 3/1989 | Cabilly et al. |
| 5,225,539 A | 7/1993 | Winter |
| 5,530,101 A | 6/1996 | Queen et al. |
| 5,565,332 A | 10/1996 | Hoogenboom et al. |
| 5,585,089 A | 12/1996 | Queen et al. |
| 5,731,168 A | 3/1998 | Carter et al. |
| 5,807,715 A | 9/1998 | Morrison et al. |
| 5,885,793 A | 3/1999 | Griffiths et al. |
| 6,248,516 B1 | 6/2001 | Winter et al. |
| 6,300,064 B1 | 10/2001 | Knappik et al. |
| 7,235,641 B2 | 6/2007 | Kufer et al. |
| 2006/0148738 A1* | 7/2006 | Muramatsu ........ A61K 31/7088 514/44 A |
| 2006/0263367 A1 | 11/2006 | Fey et al. |
| 2007/0135620 A1 | 6/2007 | Chamberlain et al. |
| 2010/0092488 A1 | 4/2010 | Suzumura et al. |

FOREIGN PATENT DOCUMENTS

| | | |
|---|---|---|
| EA | 1607102 A1 | 12/2005 |
| EP | 339568 A1 | 11/1989 |
| EP | 569141 A2 | 11/1993 |
| EP | 2088159 A1 | 8/2009 |
| JP | 2104292 A | 4/1990 |
| JP | 7039889 A | 2/1995 |
| JP | 2002085058 A | 3/2002 |
| WO | WO-94/04678 A1 | 3/1994 |
| WO | WO-94/07921 A1 | 4/1994 |
| WO | WO-97/49805 A2 | 12/1997 |
| WO | WO-98/44001 A1 | 10/1998 |
| WO | WO-99/03493 A1 | 1/1999 |
| WO | WO-99/57134 A1 | 11/1999 |
| WO | WO-00/10608 A1 | 3/2000 |
| WO | WO-00/34317 A2 | 6/2000 |
| WO | WO-02/066630 A1 | 8/2002 |
| WO | WO-2004/064724 A2 | 8/2004 |
| WO | WO-2004/078210 A1 | 9/2004 |
| WO | WO-2004/108158 A1 | 12/2004 |
| WO | WO-2005/118629 A1 | 12/2005 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Maehara et al (2007). Biochemical and Biophysical Research Communications. 358:757-762.*
"International Application No. PCT/AU2012/000251, International Search Report mailed Apr. 3, 2012", (Apr. 3, 2012), 4 pgs.
Al-Lazikani, B., et al., "Standard conformations for the canonical structures of immunoglobulins", J Mol Biol., 273(4), (Nov. 7, 1997), 927-48.
Bork, P., et al., "The immunoglobulin fold. Structural classification, sequence patterns and common core.", J Mol Biol., 242(4), (Sep. 30, 1994), 309-20.
Chothia, C., et al., "Canonical structures for the hypervariable regions of immunoglobulins.", J Mol Biol., 196(4), (Aug. 20, 1987), 901-17.
Chothia, C., et al., "Conformations of immunoglobulin hypervariable regions", Nature, 342(6252), (Dec. 28, 1989), 877-83.
Englebienne, P, "Use of colloidal gold surface plasmon resonance peak shift to infer affinity constants from the interactions between protein antigens and antibodies specific for single or multiple epitopes", Analyst, 123(7), (Jul. 1998), 1599-603.
Iwasaki, W., et al., "Solution structure of midkine, a new heparin-binding growth factor", EMBO J., 16(23), (Dec. 1, 1997), 6936-46.

(Continued)

*Primary Examiner* — Christine J Saoud
*Assistant Examiner* — Jon M Lockard
(74) *Attorney, Agent, or Firm* — Schwegman Lundberg & Woessner, P.A.

(57) ABSTRACT

The present disclosure relates to isolated or recombinant proteins, such as antibodies, which inhibit or reduce the function of midkine (hereinafter, referred to as "MK") for use in the treatment or prevention of midkine-related disorders.

11 Claims, 7 Drawing Sheets

(56) References Cited

OTHER PUBLICATIONS

Kadomatsu, K., et al., "cDNA cloning and sequencing of a new gene intensely expressed in early differentiation stages of embryonal carcinoma cells and in mid-gestation period of mouse embryogenesis", Biochem Biophys Res Commun., 151(3), (Mar. 30, 1988), 1312-8.

Kojima, S., et al., "Synthetic peptides derived from midkine enhance plasminogen activator activity in bovine aortic endothelial cells", Biochem Biophys Res Commun., 206(2), (Jan. 17, 1995), 468-73.

Kojima, Soichi, et al., "Dimerization of midkine by tissue transglutaminase and its functional implication", J Biol Chem., 272(14), (Apr. 4, 1997), 9410-6.

Largaespada, D. A, et al., "The ABL-MYC retrovirus generates antigen-specific plasmacytomas by in vitro infection of activated B lymphocytes from spleen and other murine lymphoid organs", J Immunol Methods., 197(1-2), (Oct. 16, 1996), 85-95.

Malmqvist, M, "BIACORE: an affinity biosensor system for characterization of biomolecular interactions", Biochem Soc Trans., 27(2), (Feb. 1999), 335-40.

Matsui, T., et al., "Midkine inhibitors: application of a simple assay procedure to screening of inhibitory compounds", Int Arch Med., 3, (Jun. 21, 2010), 12.

Muramatsu, H., et al., "Localization of heparin-binding, neurite outgrowth and antigenic regions in midkine molecule", Biochem Biophys Res Commun., 203(2), (Sep. 15, 1994), 1131-9.

Muramatsu, T., "Midkine and pleiotrophin: two related proteins involved in development, survival, inflammation and tumorigenesis", J Biochem., 132(3), (Sep. 2002), 359-71.

Nakamura, E., et al., "Disruption of the midkine gene (Mdk) resulted in altered expression of a calcium binding protein in the hippocampus of infant mice and their abnormal behaviour", Genes Cells, 3(12), (Dec. 1998), 811-22.

Rich, R. L, et al., "Advances in surface plasmon resonance biosensor analysis", Curr Opin Biotechnol., 11(1), (Feb. 2000), 54-61.

Tomomura, M., et al., "A retinoic acid-responsive gene, MK, found in the teratocarcinoma system. Heterogeneity of the transcript and the nature of the translation product", J Biol Chem., 265(18), (Jun. 25, 1999), 10765-70.

Tsutsui, J., et al., "A new family of heparin-binding factors: strong conservation of midkine (MK) sequences between the human and the mouse", Biochem Biophys Res Commun., 176(2), (Apr. 30, 1991), 792-7.

"European Application Serial No. 12757658.5, Search Report mailed Aug. 6, 2014", 9 pgs.

Hirota, Yasushi, et al., "The Presence of Midkine and its Possible Implications in Human Ovarian Follicles", American Journal of Reproductive Immunology 58, (2007), 367-373.

Inoh, K., et al., "Doxorubicin-Conjugated Anti-Midkine Monoclonal Antibody as a Potential Anti-Tumor Drug", Japanese Journal of Clinical Oncology, 36(4), (2006), 5 pgs.

Yao, Xing, et al., "Preparation and Preliminary Characterization of Rabbit Monoclonal Antibodies Against Human Midkine", Hybridoma 30(1), (2011), 87-93.

\* cited by examiner

Figure 1

Open circles: Control
Closed diamonds: IP-10

```
                          SEQUENCE LISTING

<160> NUMBER OF SEQ ID NOS: 14

<210> SEQ ID NO 1
<211> LENGTH: 143
<212> TYPE: PRT
<213> ORGANISM: Homo sapiens

<400> SEQUENCE: 1

Met Gln His Arg Gly Phe Leu Leu Thr Leu Ala Leu Leu Ala
1               5                   10                  15

Leu Thr Ser Ala Val Ala Lys Lys Asp Lys Val Lys Lys Gly Gly
                20                  25                  30

Pro Gly Ser Glu Cys Ala Glu Trp Ala Trp Gly Pro Cys Thr Pro Ser
                35                  40                  45

Ser Lys Asp Cys Gly Val Gly Phe Arg Glu Gly Thr Cys Gly Ala Gln
    50                  55                  60

Thr Gln Arg Ile Arg Cys Arg Val Pro Cys Asn Trp Lys Lys Glu Phe
65                  70                  75                  80

Gly Ala Asp Cys Lys Tyr Lys Phe Glu Asn Trp Gly Ala Cys Asp Gly
                85                  90                  95

Gly Thr Gly Thr Lys Val Arg Gln Gly Thr Leu Lys Lys Ala Arg Tyr
                100                 105                 110

Asn Ala Gln Cys Gln Glu Thr Ile Arg Val Thr Lys Pro Cys Thr Pro
            115                 120                 125

Lys Thr Lys Ala Lys Ala Lys Ala Lys Lys Gly Lys Gly Lys Asp
        130                 135                 140

<210> SEQ ID NO 2
<211> LENGTH: 61
<212> TYPE: PRT
<213> ORGANISM: Homo sapiens

<400> SEQUENCE: 2

Lys Lys Lys Asp Lys Val Lys Lys Gly Gly Pro Gly Ser Glu Cys Ala
1               5                   10                  15

Glu Trp Ala Trp Gly Pro Cys Thr Pro Ser Ser Lys Asp Cys Gly Val
                20                  25                  30

Gly Phe Arg Glu Gly Thr Cys Gly Ala Gln Thr Gln Arg Ile Arg Cys
            35                  40                  45

Arg Val Pro Cys Asn Trp Lys Lys Glu Phe Gly Ala Asp
        50                  55                  60

<210> SEQ ID NO 3
<211> LENGTH: 321
<212> TYPE: DNA
<213> ORGANISM: Mus musculus

<400> SEQUENCE: 3
agtattgtga tgacccagac tcccaacttc ctgcttgtat cagcaggaga cagggttacc       60
ataacctgca aggccagtca gagtgtgagt aatgatgtat cttggtacca acagaagcca      120
gggcagtctc ctaaacttct gatatactat gcatccaatc tctacactgg agtccctgat      180
cgcttcactg gcagtggata tgggacggat ttcactttca ccatcagcac tgtgcaggct      240
gaagacctgg cagtttattt ctgtcagcag gattatagct ctccgtggac gttcggtgga      300
ggcaccaagc tggaaatcaa a                                                321
```

<210> SEQ ID NO 4
<211> LENGTH: 357
<212> TYPE: DNA
<213> ORGANISM: Mus musculus

<400> SEQUENCE: 4

```
gaggtccagc tgcaacagtc tggacctgag ctggtgaagc ctggggcttc agtgaagata      60
ccctgcaagg cttctggata cacattcact gactacaaca tgggctgggt aaaacagagc     120
catggaaaga gccttgagtg gattggagat attaatccta caatggtgg tactatctac      180
aaccagaagt tcaagggcaa ggccacattg actgttgaca gtcctccag cacagcctac      240
atggaactcc gcagcctgac atctgaggac actgcagtct attactgtgc aagatggagc     300
tatagtaacc cctactttga ctactggggc caaggcacca ctctcacagt ctcctca       357
```

<210> SEQ ID NO 5
<211> LENGTH: 119
<212> TYPE: PRT
<213> ORGANISM: Mus musculus

<400> SEQUENCE: 5

```
Glu Val Gln Leu Gln Gln Ser Gly Pro Glu Leu Val Lys Pro Gly Ala
 1               5                  10                  15

Ser Val Lys Ile Pro Cys Lys Ala Ser Gly Tyr Thr Phe Thr Asp Tyr
             20                  25                  30

Asn Met Gly Trp Val Lys Gln Ser His Gly Lys Ser Leu Glu Trp Ile
         35                  40                  45

Gly Asp Ile Asn Pro Asn Asn Gly Gly Thr Ile Tyr Asn Gln Lys Phe
     50                  55                  60

Lys Gly Lys Ala Thr Leu Thr Val Asp Lys Ser Ser Thr Ala Tyr
 65                  70                  75                  80

Met Glu Leu Arg Ser Leu Thr Ser Glu Asp Thr Ala Val Tyr Tyr Cys
                 85                  90                  95

Ala Arg Trp Ser Tyr Ser Asn Pro Tyr Phe Asp Tyr Trp Gly Gln Gly
             100                 105                 110

Thr Thr Leu Thr Val Ser Ser
         115
```

<210> SEQ ID NO 6
<211> LENGTH: 107
<212> TYPE: PRT
<213> ORGANISM: Mus musculus

<400> SEQUENCE: 6

```
Ser Ile Val Met Thr Gln Thr Pro Asn Phe Leu Leu Val Ser Ala Gly
 1               5                  10                  15

Asp Arg Val Thr Ile Thr Cys Lys Ala Ser Gln Ser Val Ser Asn Asp
             20                  25                  30

Val Ser Trp Tyr Gln Gln Lys Pro Gly Gln Ser Pro Lys Leu Leu Ile
         35                  40                  45

Tyr Tyr Ala Ser Asn Leu Tyr Thr Gly Val Pro Asp Arg Phe Thr Gly
     50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Ser Ser Pro Trp
                 85                  90                  95
```

```
Thr Phe Gly Gly Gly Thr Lys Leu Glu Ile Lys
            100                 105

<210> SEQ ID NO 7
<211> LENGTH: 10
<212> TYPE: PRT
<213> ORGANISM: Mus musculus

<400> SEQUENCE: 7

Gly Tyr Thr Phe Thr Asp Tyr Asn Met Gly
1               5                   10

<210> SEQ ID NO 8
<211> LENGTH: 17
<212> TYPE: PRT
<213> ORGANISM: Mus musculus

<400> SEQUENCE: 8

Asp Ile Asn Pro Asn Asn Gly Gly Thr Ile Tyr Asn Gln Lys Phe Lys
1               5                   10                  15

Gly

<210> SEQ ID NO 9
<211> LENGTH: 10
<212> TYPE: PRT
<213> ORGANISM: Mus musculus

<400> SEQUENCE: 9

Trp Ser Tyr Ser Asn Pro Tyr Phe Asp Tyr
1               5                   10

<210> SEQ ID NO 10
<211> LENGTH: 11
<212> TYPE: PRT
<213> ORGANISM: Mus musculus

<400> SEQUENCE: 10

Lys Ala Ser Gln Ser Val Ser Asn Asp Val Ser
1               5                   10

<210> SEQ ID NO 11
<211> LENGTH: 7
<212> TYPE: PRT
<213> ORGANISM: Mus musculus

<400> SEQUENCE: 11

Tyr Ala Ser Asn Leu Tyr Thr
1               5

<210> SEQ ID NO 12
<211> LENGTH: 9
<212> TYPE: PRT
<213> ORGANISM: Mus musculus

<400> SEQUENCE: 12

Gln Gln Asp Tyr Ser Ser Pro Trp Thr
1               5

<210> SEQ ID NO 13
<211> LENGTH: 30
<212> TYPE: DNA
<213> ORGANISM: Artificial Sequence
<220> FEATURE:
<223> OTHER INFORMATION: forward primer
```

```
<400> SEQUENCE: 13
gcggaattca tgcagcaccg aggcttcctc                                        30

<210> SEQ ID NO 14
<211> LENGTH: 30
<212> TYPE: DNA
<213> ORGANISM: Artificial Sequence
<220> FEATURE:
<223> OTHER INFORMATION: reverse primer

<400> SEQUENCE: 14
gcggaattcc tagtcctttc ccttcccttt                                        30
```

ANTIBODY RECOGNIZING N-DOMAIN OF MIDKINE

PRIORITY CLAIM TO RELATED APPLICATIONS

This application is a national stage application under 35 U.S.C. §371 of PCT/AU2012/000251, filed Mar. 13, 2012, and published as WO 2012/122590 A1 on Sep. 20, 2012, which claims priority to U.S. Application No. 61/452,337, filed Mar. 14, 2011, which applications and publication are incorporated by reference as if reproduced herein and made a part hereof in their entirety, and the benefit of priority of each of which is claimed herein.

FIELD

The present disclosure relates to isolated or recombinant proteins, such as antibodies, which inhibit or reduce the function of midkine (hereinafter, referred to as "MK") for use in the treatment or prevention of midkine-related disorders.

BACKGROUND

Midkine (hereinafter, referred to as "MK") is a growth/differentiation factor found as a product of a gene transiently expressed in the stage of retinoic acid-induced differentiation of embryonal carcinoma (EC) cells and is a polypeptide of 13 kDa in molecular weight rich in basic amino acids and cysteine (Kadomatsu. et al. (1988) Biochem. Biophys. Res. Commun., 1511312-1318; Tomokura et al. (1999) J. Biol. Chem., 265:10765-10770).

MK is known to have various biological activities. For example, it is known that MK expression is increased in human cancer cells. This increase in expression has been confirmed in various cancers such as esophageal cancer, thyroid cancer, urinary bladder cancer, colon cancer, stomach cancer, pancreatic cancer, thoracic cancer, liver cancer, lung cancer, breast cancer, neuroblastoma, glioblastoma, uterine cancer, ovarian cancer, and Wilms tumor (Muramatsu (2002) J. Biochem. 132:359-371). Moreover, MK is thought to promote the survival and migration of cancer cells, promote angiogenesis, and contribute to cancer progression.

MK is also known to play a central role in the stage of inflammation formation. For example, it is known that neointimal formation after vascular injury and nephritis onset during ischemic injury are suppressed in knockout mice deficient in MK genes. Moreover, it is also known that rheumatism models and postoperative adhesion are significantly suppressed in such knockout mice (WO2000/10608; WO2004/078210). Thus, MK is known to participate in inflammatory diseases such as arthritis, autoimmune disease, rheumatic arthritis (rheumatoid arthritis (RA) or osteoarthritis (OA)), multiple sclerosis, postoperative adhesion, inflammatory bowel disease, psoriasis, lupus, asthma, and neutrophil dysfunction. Furthermore, MK is known to promote the movement (migration) of inflammatory cells such as macrophages or neutrophils. Since this movement is necessary for the establishment of inflammation, it is thought that deficiency of MK probably prevents diseases based on inflammation (WO1999/03493).

The three-dimensional structure of MK has been determined by NMR and reported (Iwasaki et al. (1997) EMBO J. 16, p. 6936-6946). MK is composed of: an N-terminal fragment (hereinafter, referred to as an "N-fragment") consisting of amino acid residues 1 to 52; a C-terminal fragment (hereinafter, referred to as a "C-fragment") consisting of amino acid residues 62 to 121; and a loop region (amino acid residues 53 to 61) (hereinafter, referred to as a "loop") that links these fragments. Each of the N- and C-fragments is mainly composed of: a portion having a three-dimensional structure consisting of three antiparallel [beta]-sheets (hereinafter, referred to as a "domain"; the domain (consisting of amino acid residues 15 to 52) in the N-fragment is referred to as an "N-domain", and the domain (consisting of amino acid residues 62 to 104) in the C-fragment is referred to as a "C-domain"); and a terminally located portion devoid of the domain that does not assume a particular three-dimensional structure (hereinafter, referred to as a "tail"; the tail (consisting of amino acid residues 1 to 14) in the N-fragment is referred to as an "N-tail", and the tail (consisting of amino acid residues 105 to 121) in the C-fragment is referred to as a "C-tail"). Basic amino acids on the C-domain surface form two clusters: a cluster consisting of lysine 79, arginine 81, and lysine 102 (cluster I) and a cluster consisting of lysine 86, lysine 87, and arginine 89 (cluster II). Both the clusters are known to participate in heparin-binding ability.

The C-terminally located domain is usually responsible for MK activity (Kojima et al. (1995) Biochem Biophys. Res. Comm. 206:468-473; Muramatsu et al. (1994) Biochem Biophys. Res. Comm. 203:1131-1139; Matsui et al. (2010) Int. Arch Medicine 3:12). Development of anti-MK antibodies has therefore focused on antibodies which are directed against the C-domain.

SUMMARY

The present inventors have prepared antibodies against the N-domain of human MK and made the surprising finding that these antibodies inhibit the cell migration function of MK to a substantially greater extent than antibodies directed against the MK C-domain. An exemplary antibody of the invention has also been shown to have excellent inhibitory effects on the onset of Experimental Autoimmune Encephalomyelitis (EAE) in a mouse model.

Accordingly, the present disclosure provides a method for treating or preventing a midkine-related disorder comprising administering to a subject in need thereof an isolated or recombinant protein comprising an antigen binding domain of an antibody which specifically binds to an epitope located within the N-domain of midkine (MK) as defined by amino acid residues 1-61 of SEQ ID NO:2, wherein the protein inhibits or reduces a function of MK.

The present disclosure also provides an isolated or recombinant protein comprising an antigen binding domain of an antibody which specifically binds to an epitope located within the N-domain of midkine (MK) as defined by amino acid residues 1-61 of SEQ ID NO:2, for use in the treatment of prevention of a midkine-related disorder wherein the protein inhibits or reduces a function of MK.

In one example the isolated or recombinant protein inhibits or reduces the cell migratory function of midkine.

In one example the isolated or recombinant protein specifically binds to a conformational epitope formed by the protein of SEQ ID NO:2, wherein the epitope includes at least two residues selected from the group consisting of 18W; 20W; 34F; 35R, 36E, 38T, 43T, 45R, 47R and 49R. For example, the epitope may be defined by the following residues:

(i) 18W, 20W, 35R and 49R;
(ii) 19W, 20W, 36E, 38T, 43T and 45R; or
(iii) 18W, 20W, 34F, 36E, 45R and 47R.

In another example the isolated or recombinant protein binds to the same epitope as monoclonal antibody IP-13 or to an overlapping epitope.

In another example the isolated or recombinant protein comprises at least one variable domain of an antibody.

For example, the isolated or recombinant protein may comprise a heavy chain variable domain comprising a complementarity determining region 3 (CDR3) sequence as shown in SEQ ID NO: 9 or a sequence exhibiting 95% or greater identity thereto.

The heavy chain variable domain may further comprise a CDR1 sequence as shown in SEQ ID NO: 7 or a sequence exhibiting 95% or greater identity thereto and a CDR2 sequence as shown in SEQ ID NO:8 or a sequence exhibiting 95% or greater identity thereto.

In one example the heavy chain variable domain comprises the sequence as shown in SEQ ID NO: 5 or a sequence exhibiting 95% or greater identity thereto.

In another example the isolated or recombinant protein comprises a light chain variable domain comprising a CDR3 sequence as shown in SEQ ID NO: 12 or a sequence exhibiting 95% or greater identity thereto.

The light chain variable domain may further comprise a CDR1 sequence as shown in SEQ ID NO: 10 or a sequence exhibiting 95% or greater identity thereto and a CRD2 sequence as shown in SEQ ID NO:11 or a sequence exhibiting 95% or greater identity thereto.

In one example the light chain variable domain comprises a sequence as shown in SEQ ID NO: 6 or a sequence exhibiting 95% or greater identity thereto.

In another example the isolated or recombinant protein comprises a heavy chain variable domain (VH) and a light chain variable domain (VL).

The VH and the VL may be in the form of a single polypeptide chain, such as in the form of;
  (i) a single chain Fv fragment (scFv);
  (ii) a dimeric scFv (di-scFv); or
  (iii) at least one of (i) and/or (ii) linked to a Fc or a heavy chain constant domain (CH)2 and/or CH3.

In another example the VL and VH are in separate polypeptide chains, such as in the form of:
  (i) a diabody;
  (ii) a triabody;
  (iii) a tetrabody;
  (iv) a Fab;
  (v) a F(ab')2;
  (vi) a Fv; or
  (iv) one of (i) to (iii) linked to a Fc or a heavy chain constant domain (CH)2 and/or CH3.

In one example the isolated or recombinant protein is a chimeric, de-immunized, humanized or human antibody.

In another example the isolated or recombinant protein comprises a human or non-human primate heavy chain immunoglobulin constant region selected from a group consisting of IgG1, IgG2, IgG3, IgG4, IgM, IgE and IgA.

In another example the isolated or recombinant protein is in the form of an antibody comprising:
  a heavy chain variable domain comprising heavy chain CDR sequences CDR1, CDR2 and CDR3 as shown in SEQ ID NO: 7, SEQ ID NO: 8 and SEQ ID NO: 9 respectively; and
  a light chain variable domain comprising light chain CDR sequences CDR1, CD2 and CDR3 as shown in SEQ ID NO: 10, SEQ ID NO: 11 and SEQ ID NO: 12 respectively;
  wherein the protein inhibits or reduces a function of MK.

In another example the isolated or recombinant protein is in the form of an antibody comprising:
  a heavy chain variable domain comprising SEQ ID NO: 5 or a sequence exhibiting 95% or greater identity thereto; and
  a light chain variable domain comprising SEQ ID NO: 6 or a sequence exhibiting 95% or greater identity thereto, or a light chain variable domain comprising SEQ ID NO:8 or a sequence exhibiting 95% or greater identity thereto,
  wherein the protein inhibits or reduces a function of MK.

The isolated or recombinant protein may be conjugated to a compound. For example, the compound may be selected from the group consisting of a radioisotope, a detectable label, a therapeutic compound, a colloid, a toxin, a nucleic acid, a peptide, a protein, a compound that increases the half life of the protein in a subject and mixtures thereof.

The present disclosure also provides for administration of the isolated or recombinant protein by way of an isolated or recombinant nucleic acid molecule encoding the protein. The isolated or recombinant nucleic acid molecule may be operably linked to a promoter in the form of an expression construct.

The present disclosure also provides for administration of the isolated or recombinant protein in the form of a composition comprising the protein or the nucleic acid molecule or the expression construct as described above and a suitable carrier or diluent.

The present disclosure also encompasses the use of the protein or the nucleic acid or the expression construct or the composition of the present disclosure in medicine.

The MK-related disorder may be, for example, an autoimmune disease, cancer, an inflammatory disease or multiple sclerosis.

In one example, the method comprises administering between about 0.0001 mg/kg and 50 mg/kg of protein to the mammal. For example, the method comprises administering between about 0.0005 mg/kg to about 50 mg/kg.

In one example, the protein is administered at a dose of about 0.1 mg/kg, or at a dose of about 1 mg/kg, or at a dose of about 10 mg/kg, or at a dose of about 30 mg/kg.

The present disclosure also provides a method for detecting MK in a sample, the method comprising contacting a sample with the protein of the disclosure such that a MK-protein complex forms and detecting the complex, wherein the complex is indicative of MK in the sample.

It will be appreciated that the method for detecting MK in a sample may be used for diagnosing a MK-related condition in a subject, wherein detection of MK in the sample is indicative of the condition. For example, an increased or decreased level of MK in the sample compared to a control sample may be indicative of the condition.

Suitably, according to the aforementioned examples of the present disclosure, the mammal is a human.

Other objects, examples and advantages will become apparent from the following detailed description. The detailed description and specific examples are given for illustration only since various changes and modifications within the spirit and scope of the present disclosure will become apparent to those skilled in the art from this detailed description. Further, the examples demonstrate the principle of methods disclosed in the present disclosure and do not specifically illustrate the application of the present disclosure to all the examples where it will be obviously useful to those skilled in the prior art.

BRIEF DESCRIPTION OF THE FIGURES

FIG. 1: Epitopic residues of IP-9, IP-10 and IP-13.

DETAILED DESCRIPTION

Figure 2:
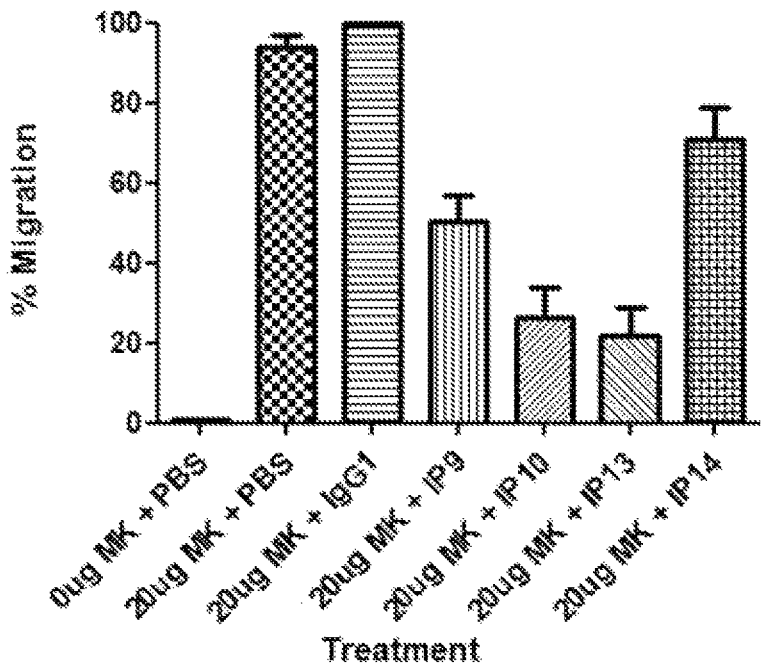
FIG. 2: Inhibition of MK-mediated migration of UMR106 cells by anti-MK mAbs.

Key to Sequence Listing
SEQ ID NO 1: full length amino acid sequence *Homo sapiens* midkine (including signal sequence (residues 1-22)
SEQ ID NO 2: amino acid sequence of the N-domain (1-61) of *Homo sapiens* midkine
SEQ ID NO 3: DNA sequence encoding the light chain variable domain of IP-13
SEQ ID NO 4: DNA sequence encoding the heavy chain variable domain of IP-13
SEQ ID NO 5: amino acid sequence of the heavy chain variable domain of IP-13
SEQ ID NO 6: amino acid sequence of the light chain variable domain of IP-13
SEQ ID NO 7: amino acid sequence of IP-13 CDR H1
SEQ ID NO 8: amino acid sequence of IP-13 CDR H2
SEQ ID NO 9: amino acid sequence of IP-13 CDR H3
SEQ ID NO 10: amino acid sequence of IP-13 CDR L1
SEQ ID NO 11: amino acid sequence of IP-13 CDR L2
SEQ ID NO 12: amino acid sequence of IP-13 CDR L3
SEQ ID NO 13: sense primer for preparing human MK mRNA
SEQ ID NO 14: anti-sense primer for preparing human MK mRNA.

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health, Bethesda, Md., 1987 and 1991, Bork et al., *J. Mol. Biol.* 242, 309-320, 1994, Chothia and Lesk *J. Mol. Biol.* 196:901-917, 1987, Chothia et al. *Nature* 342, 877-883, 1989 and/or or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

The skilled artisan will be aware that an "antibody" is generally considered to be a protein that comprises a variable region made up of a plurality of polypeptide chains, e.g., a polypeptide comprising a $V_L$ and a polypeptide comprising a $V_H$. An antibody also generally comprises constant domains, some of which can be arranged into a constant region or constant fragment or fragment crystallizable (Fc). A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, de-immunized antibodies, primatized antibodies, human antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof. In some cases, the intact antibody may have one or more effector functions.

An "antigen binding fragment" of an antibody comprises the antigen binding and/or the variable region of the intact antibody. Examples of antibody fragments include Fab, Fab', F(ab')$_2$ and Fv fragments; diabodies; linear antibodies; single-chain antibody molecules and multispecific antibodies formed from antibody fragments.

As used herein, "variable region" refers to the portions of the light and/or heavy chains of an antibody as defined herein that is capable of specifically binding to an antigen and, for example, includes amino acid sequences of CDRs; i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain. The amino acid positions assigned to CDRs and FRs can be defined according to Kabat (1987 and 1991, supra) or other numbering systems in the performance of methods according to the present disclosure, e.g., the hypervariable loop numbering system of Clothia and Lesk (1987 and/or 1989, supra and/or Al-Lazikani et al., 1997, supra). For example, according to the numbering system of Kabat, a $V_H$ FRs and CDRs positioned as follows residues 1-30 (FR1), 31-25 (CDR1), 36-49 (FR2), 50-65 (CDR2), 66-94 (FR3), 95-102 (CDR3) and 103-113 (FR4), numbered according to the Kabat numbering system. For example, according to the numbering system of Kabat, a $V_L$ FRs and CDRs are positioned as follows residues 1-23 (FR1), 24-34 (CDR1), 35-49 (FR2), 50-56 (CDR2), 57-88 (FR3), 89-97 (CDR3) and 98-107 (FR4).

As used herein, the term "complementarity determining regions" (syn. CDRs; i.e., CDR1, CDR2, and CDR3) refers to the amino acid residues of an antibody variable domain that form loops between the FRs the sequence of which vary between antibodies. Some or all of the CDRs confer the ability to bind antigen on the antibody. Each variable domain typically has three CDR regions identified as CDR1, CDR2 and CDR3. Each complementarity determining region may comprise amino acid residues from a "complementarity determining region" as defined by Kabat et al., (1991) and/or those residues from a "hypervariable loop" Chothia and Lesk (1987), or any other known numbering technique or combination thereof, including the IMGT numbering system (Le Franc et al., 2003).

"Framework regions" (hereinafter FR) are those variable domain residues other than the CDR residues.

The term "constant region" or "fragment crystallizable" or "Fc" or "Fc region" or "Fc portion" (which can be used interchangeably herein) as used herein, refers to a portion of an antibody comprising at least one constant domain and which is generally (though not necessarily) glycosylated and which is capable of binding to one or more Fc receptors and/or components of the complement cascade. The heavy chain constant region can be selected from any of the five isotypes: α, δ, ε, γ, or μ. Furthermore, heavy chains of various subclasses (such as the IgG subclasses of heavy chains) are responsible for different effector functions and thus, by choosing the desired heavy chain constant region, proteins with desired effector function can be produced. Exemplary heavy chain constant regions are gamma 1 (IgG1), gamma 2 (IgG2) and gamma 3 (IgG3), or hybrids thereof.

A "constant domain" is a domain in an antibody the sequence of which is highly similar in antibodies/antibodies of the same type, e.g., IgG or IgM or IgE. A constant region of an antibody generally comprises a plurality of constant domains, e.g., the constant region of γ, α and δ heavy chains comprises two constant domains.

As used herein, the term "specifically binds" shall be taken to mean a protein reacts or associates more frequently, more rapidly, with greater duration and/or with greater affinity with midkine or a specified epitope thereof than it does with alternative antigens or epitopes. As such, "specific binding" does not necessarily require exclusive binding or non-detectable binding of another antigen. The term specifically binds" is used interchangeably with "selectively binds" herein.

The term "competitively inhibits" shall be understood to mean that a isolated or recombinant protein such as an antibody reduces or prevents binding of the monoclonal antibody designated IP-13 to human midkine. It will be apparent from the foregoing that the antibody need not completely inhibit binding of the monoclonal antibody IP-13, rather it need only reduce binding by a statistically significant amount, for example, by at least about 10% or 20% or 30% or 40% or 50% or 60% or 70% or 80% or 90% or 95%. Methods for determining competitive inhibition of binding are known in the art and/or described herein. For example, monoclonal antibody IP-13 is exposed to mdikine either in the presence or absence of the recombinant protein. If less monoclonal antibody binds in the presence of the recombinant protein than in the absence of it, the recombinant protein is considered to competitively inhibit binding of monoclonal antibody IP-13 to midkine.

By "overlapping" in the context of two epitopes shall be taken to mean that two epitopes share a sufficient number of amino acid residues to permit an antibody that binds to one epitope to competitively inhibit the binding of an antibody that binds to the other epitope. For example, the two epitopes share at least 1 or 2 or 3 or 4 or 5 or 6 or more amino acids.

Reference herein to "monoclonal antibody IP-13" or to "IP-13" is a reference to the monoclonal antibody which has a variable heavy chain sequence as shown in SEQ ID NO:5 and a variable light chain sequence as shown in SEQ ID NO:6.

The term "EU numbering system of Kabat" will be understood to mean the numbering of an immunoglobulin heavy chain is according to the EU index as taught in Kabat et al., 1991, Sequences of Proteins of Immunological Interest, 5th Ed., United States Public Health Service, National Institutes of Health, Bethesda. The EU index is based on the residue numbering of the human IgG1 EU antibody.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease (e.g., lupus) are mitigated or eliminated.

As used herein, the term "prevention" includes providing prophylaxis with respect to occurrence or recurrence of a disease in an individual. An individual may be predisposed to or at risk of developing the disease or disease relapse but has not yet been diagnosed with the disease or the relapse.

The term prevention does not require absolute prevention but includes inhibiting the progression of the disease to some extent.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is meant an amount necessary to effect treatment of a disease or condition as hereinbefore described. The effective amount may vary according to the disease or condition to be treated and also according to the weight, age, racial background, sex, health and/or physical condition and other factors relevant to the mammal being treated. Typically, the effective amount will fall within a relatively broad range (e.g. a "dosage" range) that can be determined through routine trial and experimentation by a medical practitioner. The effective amount can be administered in a single dose or in a dose repeated once or several times over a treatment period.

A "therapeutically effective amount" is at least the minimum concentration required to effect a measurable improvement of a particular disorder (e.g., MS). A therapeutically effective amount herein may vary according to factors such as the disease state, age, sex, and weight of the patient, and the ability of the protein to elicit a desired response in the individual. A therapeutically effective amount is also one in which any toxic or detrimental effects of the protein are outweighed by the therapeutically beneficial effects.

A "prophylactically effective amount" refers to an amount effective, at the dosages and for periods of time necessary, to achieve the desired prophylactic result. Typically but not necessarily, since a prophylactic dose is used in mammals prior to or at an earlier stage of disease, a prophylactically effective amount may be less than a therapeutically effective amount.

For the purposes of nomenclature only and not limitation, the amino acid sequence of human midkine is shown in SEQ ID NO: 1 and the N-domain sequence is shown in SEQ ID NO:2.

The "mammal" treated according to the present disclosure may be a primate, livestock (e.g. sheep, horses, cattle, pigs, donkeys), companion animal (e.g. pets such as dogs and cats), laboratory test animal (e.g. mice, rabbits, rats, guinea pigs), performance animal (e.g. racehorses, camels, greyhounds) or captive wild animal. In one example, the mammal is a human.

Monoclonal Antibody IP-13
Protein Sequences

The present disclosure provides antibodies and functional antigen-binding fragments that are structurally and/or functionally related to IP-13, in which the heavy chain variable region sequence exhibits a degree of identity to SEQ ID NO:5 and the light chain variable region sequence exhibits a degree of identity to SEQ ID NO:6. In particular embodiments, antibodies and antigen-binding fragments include a heavy or a light chain variable region sequence with about 80% or more identity to a heavy or light chain sequence variable region of IP-13 or a sequence within the variable region (e.g., one or more CDRs). In other particular embodiments, antibodies or antigen-binding fragments include a heavy or a light chain with at least 82%, 85%, 90%, 95%, or more identity to a heavy chain variable region sequence of IP-13, or a sequence within the variable region (e.g., one or more CDRs). In additional particular embodiments, antibodies or antigen-binding fragments include a heavy or a light chain variable region sequence with at least 80-85%, 85-90%, 90-95%, 95-100% identity to one or more CDRs in the IP-13. In a particular example, an antibody or antigen-binding fragment thereof includes a heavy or a light chain variable region sequence with 95-100% identity to one, two or three CDRs in each heavy or light chain variable region sequence in the IP-13 antibody.

Antibodies and antigen-binding fragments of the invention therefore include those with at least partial sequence identity to IP-13. The percent identity of such antibodies and functional fragments can be as little as 80%, or can be more (e.g., 82%, 85%, 90%, 95%, 96%, 97%, 98%, 99% etc.).

The percent identity can extend over the entire sequence length of an IP-13 variable domain, or a contiguous region or area within an IP-13 variable domain. In particular aspects, the length of the sequence sharing the percent identity is 5 or more contiguous amino acids, e.g., 5, 6, 7, 8, 9, 10, 11, 12, 13, 14, 15, 16, 17, 18, 19, 20, 21, 22, 23, 24, 25, etc. contiguous amino acids. In additional particular aspects, the length of the sequence sharing the percent identity is 25 or more contiguous amino acids, e.g., 26, 27, 28, 29, 30, 31, 32, 33, 34, 35, etc. contiguous amino acids. In further particular examples, the length of the sequence sharing the percent identity is 35 or more contiguous amino acids, e.g., 35, 36, 37, 38, 39, 40, 41, 42, 43, 44, 45, 45, 47, 48, 49, 50, etc., contiguous amino acids. In yet additional particular examples, the length of the sequence sharing the percent identity is 50 or more contiguous amino acids, e.g., 50-55, 55-60, 60-65, 65-70, 70-75, 75-80, 80-85, 85-90, 90-95, 95-100, 100-110, etc. contiguous amino acids. In yet further particular examples, the length of the sequence sharing the percent identity is equal to the length of any CDR of a variable region sequence, or a region outside the CDRs but within the variable region of a heavy or light chain sequence.

In one example the CDR regions of the anti-N-domain antibody will be either identical to highly homologous to the specified regions of SEQ ID NOs: 7 to 12. By "highly homologous" it is contemplated that only a few substitutions, preferably 1, 2 or 3 substitutions may be made in the CDRs.

In one example the % identity of a full length nucleic acid or polypeptide is determined by GAP (Needleman and Wunsch, 1970) analysis (GCG program) with a gap creation penalty=5, and a gap extension penalty=0.3. The query sequence is at least 50 residues in length, and the GAP analysis aligns the two sequences over a region of at least 50 residues. Even more preferably, the query sequence is at least 100 residues in length and the GAP analysis aligns the two sequences over a region of at least 100 residues. Most preferably, the two sequences are aligned over their entire length.

Antibodies and functional fragments of the invention include those that retain at least one or more partial activities or functions of IP-13, such as the ability to inhibit midkine induce cell migration. Such antibodies include those that have greater than, about the same or less than the binding affinity of IP-13 for binding to midkine.

Binding affinity can be determined by association (Ka) and dissociation (Kd) rate. Equilibrium affinity constant, K, is the ratio of Ka/Kd. Association (Ka) and dissociation (Kd) rates can be measured using surface plasmon resonance (SPR) (Rich and Myszka, *Curr. Opin. Biotechnol.* 11:54 (2000); *Englebienne, Analyst.* 123:1599 (1998)). Instrumentation and methods for real time detection and monitoring of binding rates are known and are commercially available (BiaCore 2000, Biacore AB, Upsala, Sweden; and Malmqvist, *Biochem. Soc. Trans.* 27:335 (1999)).

Nucleic Acid Sequences

The present disclosure also provides isolated and purified nucleic acids encoding the anti-N-domain antibodies disclosed herein. Nucleic acids of the invention include, among other things, nucleic acid sequences 1) encoding antibodies that are structurally or functionally related to IP-13; 2) encoding SEQ ID NO:5 and/or SEQ ID NO: 6, or antibodies that include all or a portion of a sequence of SEQ ID NO:5 and/or SEQ ID NO: 6 (e.g., one or more CDRs); 3) that exhibit a degree of complementarity or identity with nucleic acid sequences encoding antibodies with sequence identity to IP-13; and 4) that hybridize to sequences encoding antibodies that have sequence identity to the IP-13.

For example, nucleic acid sequence encompassed by the present disclosure are 75-100% complementary or identical to a nucleic acid sequence as shown in SEQ ID NO: 3, SEQ ID NO: 4 or SEQ ID NO: 5.

The present disclosure also provides nucleic acid sequences that hybridize to a nucleic acid sequence as shown in any one of SEQ ID NOs:3 or 4. In one embodiment, a nucleic acid sequence specifically hybridizes to a nucleic acid encoding SEQ ID NO:5 (i.e. that hybridizes to a sequence as set forth in SEQ ID NO:4) or a portion thereof. In another embodiment, a nucleic acid sequence specifically hybridizes to a nucleic acid encoding SEQ ID NO:6 (i.e. that hybridizes to a sequence as set forth in SEQ ID NO:3) or a portion thereof. In a further embodiment, a nucleic acid sequence is at least 75-100% complementary or homologous to a nucleic acid sequence that encodes all or a subsequence or fragment of IP-13.

The term "hybridize" and grammatical variations thereof refer to the binding between nucleic acid sequences. Hybridizing sequences will generally have more than about 50% homology (e.g., 50%, 60%, 70%, 80%, 90%, or more identity) to a reference nucleic acid or a sequence complementary to a reference sequence. Hybridizing sequences that are 100% or fully complementary to a reference sequence, for example, to a nucleic acid that encodes an amino acid sequence of a reference sequence, exhibit 100% base pairing with no mismatches. The hybridization region between hybridizing sequences typically is at least about 12-15 nucleotides, 15-20 nucleotides, 20-30 nucleotides, 30-50 nucleotides, 50-100 nucleotides, 100 to 200 nucleotides or more, or any numerical value or range within or encompassing such lengths.

In the context of the present disclosure high stringency hybridization and/or wash conditions are preferred. A high stringency is defined herein as being a hybridization and/or wash carried out in about 0.1×SSC buffer and/or about 0.1% (w/v) SDS, or lower salt concentration, and/or at a temperature of at least 65° C., or equivalent conditions. Reference herein to a particular level of stringency encompasses equivalent conditions using wash/hybridization solutions other than SSC known to those skilled in the art.

Generally, the stringency is increased by reducing the concentration of SSC buffer, and/or increasing the concentration of SDS and/or increasing the temperature of the hybridization and/or wash. Those skilled in the art will be aware that the conditions for hybridization and/or wash may vary depending upon the nature of the hybridization matrix used to support the sample DNA, and/or the type of hybridization probe used and/or constituents of any buffer used in a hybridization. For example, formamide reduces the melting temperature of a probe or primer in a hybridization or an amplification reaction.

Conditions for specifically hybridizing nucleic acid, and conditions for washing to remove non-specific hybridizing nucleic acid, are understood by those skilled in the art. For the purposes of further clarification only, reference to the parameters affecting hybridization between nucleic acid molecules is found in Ausubel et al. (Current Protocols in Molecular Biology, Wiley Interscience, ISBN 047150338, 1992), which is herein incorporated by reference.

Nucleic acid sequences further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode, modified forms and variants thereof.

The nucleic acids of the invention can be of various lengths. Nucleic acid lengths typically range from about 20 nucleotides to 20 Kb, or any numerical value or range within or encompassing such lengths, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length, or any numerical value or range or value within or encompassing such lengths. In particular embodiments, a nucleic acid sequence has a length from about 10-20, 20-30, 30-50, 50-100, 100-150, 150-200, 200-250, 250-300, 300-400, 400-500, 500-1000, 1000-2000, nucleotides, or any numerical value or range within or encompassing such lengths.

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as yeast or bacteria, a eukaryote such as an animal or mammalian cell or in a plant).

Production of Antibodies

Methods for generating antibodies are known in the art and/or described in Harlow and Lane (editors) Antibodies: A Laboratory Manual, Cold Spring Harbor Laboratory, (1988). Generally, in such methods a midkine protein or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (Mabs).

Monoclonal antibodies are one exemplary form of antibody contemplated by the present disclosure. The term "monoclonal antibody" or "MAb" refers to a homogeneous antibody population capable of binding to the same antigen(s), for example, to the same epitope within the antigen. This term is not intended to be limited as regards to the source of the antibody or the manner in which it is made.

For the production of Mabs any one of a number of known techniques may be used, such as, for example, the procedure exemplified in U.S. Pat. No. 4,196,265 or Harlow and Lane (1988), supra.

For example, a suitable animal is immunized with an immunogen under conditions sufficient to stimulate antibody producing cells. Rodents such as rabbits, mice and rats are exemplary animals. Mice genetically-engineered to express human immunoglobulin proteins and, for example, do not express murine immunoglobulin proteins, can also be used to generate an antibody of the present disclosure (e.g., as described in WO2002/066630).

Following immunization, somatic cells with the potential for producing antibodies, specifically B lymphocytes (B cells), are selected for use in the MAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like).

Alternatively, ABL-MYC technology (NeoClone, Madison Wis. 53713, USA) is used to produce cell lines secreting MAbs (e.g., as described in Largaespada et al, *J. Immunol. Methods.* 197: 85-95, 1996).

Antibodies can also be produced or isolated by screening a display library, e.g., a phage display library, e.g., as described in U.S. Pat. Nos. 6,300,064 and/or 5,885,793.

Chimeric Antibodies

In one example an antibody described herein is a chimeric antibody. The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass. Typically chimeric antibodies utilize rodent or rabbit variable regions and human constant regions, in order to produce an antibody with predominantly human domains. Methods for producing chimeric antibodies are described in, e.g., U.S. Pat. No. 4,816,567; and U.S. Pat. No. 5,807,715.

The present disclosure also includes a chimeric immunoglobulin, e.g., in which a variable region from one species is fused to a region of a protein from another species. For example, the disclosure contemplates an immunoglobulin comprising a variable region from a T cell receptor of one species fused to a T cell receptor constant domain from a separate species.

Humanized and Human Antibodies

The antibodies of the present disclosure may be humanized or human.

The term "humanized antibody" shall be understood to refer to a subclass of chimeric antibodies having an antigen binding site or variable region derived from an antibody from a non-human species and the remaining antibody structure of the molecule based upon the structure and/or sequence of a human antibody. The antigen-binding site comprises the complementarity determining regions (CDRs) from the non-human antibody grafted onto appropriate FRs in the variable domains of a human antibody and the remaining regions from a human antibody. Antigen binding sites may be wild type or modified by one or more amino acid substitutions. In some instances, FR residues of the human immunoglobulin are replaced by corresponding non-human residues.

Methods for humanizing non-human antibodies or parts thereof (e.g., variable regions) are known in the art. Humanization can be performed following the method of U.S. Pat. Nos. 5,225,539, or 5,585,089. Other methods for humanizing an antibody are not excluded.

The term "human antibody" as used herein in connection with antibodies refers to antibodies having variable regions (e.g. $V_H$, $V_L$) and, optionally constant regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the antibody, e.g. in 1, 2, 3, 4 or 5 of the residues of the antibody, e.g. in 1, 2, 3, 4 or 5 of the residues making up one or more of the CDRs of the antibody). These "human antibodies" do not actually need to be produced by a human, rather, they can be produced using recombinant means and/or isolated from a transgenic animal (e.g., mouse) comprising nucleic acid encoding human antibody constant and/or variable regions (e.g., as described above). Human antibodies can be produced using various techniques known in the art, including phage display libraries (e.g., as described in U.S. Pat. No. 5,885,793).

Human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (e.g., as described in U.S. Pat. No. 5,565,332).

De-immunized Antibodies

The present disclosure also contemplates a de-immunized antibody or protein. De-immunized antibodies and proteins have one or more epitopes, e.g., B cell epitopes or T cell epitopes removed (i.e., mutated) to thereby reduce the likelihood that a mammal will raise an immune response against the antibody or protein. Methods for producing de-immunized antibodies and proteins are known in the art and described, for example, in WO00/34317, WO2004/108158 and WO2004/064724.

Methods for introducing suitable mutations and expressing and assaying the resulting protein will be apparent to the skilled artisan based on the description herein.

Heavy Chain Antibodies

Heavy chain antibodies differ structurally from many other forms of antibodies, in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain antibodies are generally referred to as "$V_{HH}$ domains" in camelid antibodies and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

A general description of heavy chain antibodies from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005/118629.

Antibody Fragments

Single-Domain Antibodies

In some examples, an immunoglobulin of the disclosure is or comprises a single-domain antibody (which is used interchangeably with the term "domain antibody" or "dAb"). A single-domain antibody is a single polypeptide chain comprising all or a portion of the heavy chain variable domain of an antibody. In certain examples, a single-domain antibody is a human single-domain antibody (Domantis, Inc., Waltham, Mass.; see, e.g., U.S. Pat. No. 6,248,516).

Diabodies, Triabodies, Tetrabodies

In some examples, an immunoglobulin of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

A diabody, triabody, tetrabody, etc capable of inducing effector activity can be produced using an antigen binding domain capable of binding to IL-3Rα and an antigen binding domain capable of binding to a cell surface molecule on an immune cell, e.g., a T cell (e.g., CD3).

Single Chain Fv (scFv) Fragments

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with (Gly$_4$Ser)$_3$ being one of the more favored linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present disclosure encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

The present disclosure also contemplates a dimeric scFv capable of inducing effector activity. For example, one scFv binds to IL-3Rα and another scFv binds to a cell surface molecule on an immune cell, e.g., a T cell (e.g., CD3). In one example, the dimeric protein is a combination of a dAb and a scFv. Examples of bispecific antibody fragments capable of inducing effector function are described, for example, in U.S. Pat. No. 7,235,641.

Other Antibodies and Antibody Fragments

The present disclosure also contemplates other antibodies and antibody fragments, such as:
(i) "key and hole" bispecific proteins as described in U.S. Pat. No. 5,731,168;
(ii) heteroconjugate proteins, e.g., as described in U.S. Pat. No. 4,676,980;
(iii) heteroconjugate proteins produced using a chemical cross-linker, e.g., as described in U.S. Pat. No. 4,676,980; and
(iv) Fab$_3$ (e.g., as described in EP19930302894).

Fc Regions

The present disclosure encompasses immunoglobulins comprising a Fc region of an antibody, including antigen binding fragments of an immunoglobulin fused to a Fc.

Sequences of Fc regions useful for producing the proteins of the present disclosure may be obtained from a number of different sources. In some examples, the Fc or portion thereof of the protein is derived from a human antibody. Moreover, the Fc or portion thereof may be derived from any antibody class, including IgM, IgG, IgD, IgA and IgE, and any antibody isotype, including IgG1, IgG2, IgG3 and IgG4. In one example, the Fc is human isotype IgG1 or human isotype IgG2 or human isotype IgG3 or a hybrid of any of the foregoing.

Additional Modifications

The present disclosure also contemplates additional modifications to an antibody.

For example, the antibody comprises one or more amino acid substitutions that increase its half-life. For example, the immunoglobulin comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half life of an immunoglobulin, by reducing clearance from the blood.

Exemplary amino acid substitutions include T250Q and/or M428L according to the EU numbering system of Kabat. Additional or alternative amino acid substitutions are described, for example, in US20070135620.

Recombinant Expression

In one example, an antibody encompassed by the present disclosure is produced by recombinant techniques.

In the case of a recombinant protein, nucleic acid encoding same can be cloned into expression vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce immunoglobulin protein. Exemplary cells used for expressing an immunoglobulin are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art. See U.S. Pat. Nos. 4,816,567 or 5530101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding an immunoglobulin (e.g., derived from the information provided herein), an enhancer element, a promoter, and a transcription termination sequence. The skilled artisan will be aware of suitable sequences for expression of an immunoglobulin. Exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the immunoglobulin may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Antibodies

Methods for purifying an antibody are known in the art and/or described herein.

Where an immunoglobulin is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The immunoglobulin prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbour Laboratory, (1988).

The skilled artisan will also be aware that an antibody can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting immunoglobulin is then purified using methods known in the art, such as, affinity purification. For example, an immunoglobulin comprising a hexa-his tag is purified by contacting a sample comprising the immunoglobulin with nickel-nitrilotriacetic acid (Ni-NTA) that specifically binds a hexa-his tag immobilized on a solid or semi-solid support, washing the sample to remove unbound immunoglobulin, and subsequently eluting the bound immunoglobulin. Alternatively, or in addition a ligand or antibody that binds to a tag is used in an affinity purification method.

Assaying Activity of an Antibody

Determining Competitive Binding

Assays for determining whether a test protein or antibody competitively inhibits binding of monoclonal antibody IP-13 will be apparent to the skilled artisan. For example, IP-13 may be conjugated to a detectable label, e.g., a fluorescent label or a radioactive label. The labeled IP-13 and the test antibody are then mixed and contacted with midkine or an epitope thereof. The level of labeled IP-13 is then determined and compared to the level determined when the labeled antibody is contacted with the midkine, epitope or cells in the absence of the test antibody. If the level of labeled IP-13 is reduced in the presence of the test protein compared to the absence of the test protein, the test protein is considered to competitively inhibit binding of IP-13 to midkine.

Optionally, the test antibody is conjugated to different label to IP-13. This alternate labeling permits detection of the level of binding of the test antibody to midkine or the epitope or cell.

In another example, the test antibody is permitted to bind to midkine prior to contacting the midkine with IP-13. A reduction in the amount of bound IP-13 in the presence of the test antibody compared to in the absence of the test antibody indicates that the immunoglobulin competitively inhibits IP-13 binding to midkine. A reciprocal assay can also be performed using labeled test antibody and first allowing IP-13 to bind to midkine. In this case, a reduced amount of labeled test protein bound to midkine in the presence of IP-13 compared to in the absence of IP-13 indicates that the test protein competitively inhibits binding of IP-13 to midkine.

In another example, the epitope bound by the test antibody is mapped to determine if it is the same or overlaps with the epitope bound by IP-13. Epitope mapping methods will be apparent to the skilled artisan. For example, a series of overlapping peptides spanning the midkine sequence, e.g., peptides comprising 10-15 amino acids are produced. The test antibody is then contacted to each peptide and the peptide(s) to which it binds determined. This permits determination of peptide(s) comprising the epitope to which the test antibody binds. If multiple non-contiguous peptides are bound by the test antibody the test antibody may bind a conformational epitope.

Alternatively, or in addition, amino acid residues within midkine are mutated, e.g., by alanine scanning mutagenesis, and mutations that reduce or prevent test antibody and/or IP-13 binding are determined. Any mutation that reduces or prevents binding of the test antibody is likely to be within the epitope bound by the test protein.

Alternatively, or in addition, the test antibody is produced using the epitope to which IP-13 binds, and thus is likely to bind to the same epitope.

Optionally, the dissociation constant (Kd) of a test antibody for midkine or an epitope thereof is determined. The "Kd" or "Kd value" for a midkine binding antibody is in one example measured by a radiolabeled midkine binding assay (RIA). This assay equilibrates the test antibody with a minimal concentration of radioactive midkine in the presence of a titration series of unlabeled midkine. Following washing to remove unbound midkine, the amount of radioactivity is determined, which is indicative of the Kd of the test antibody.

According to another example the Kd or Kd value is measured by using surface plasmon resonance assays, e.g., using BIAcore surface plasmon resonance (BIAcore, Inc., Piscataway, N.J.) with immobilized IL-3Rα.

In some examples, test antibodies having a similar Kd or a higher Kd than IP-13 are selected, because they are likely to compete for binding to midkine.

In Vitro Assays

Various in vitro assays are available to assess the ability of an antibody to treat a MK-related disease or condition.

For example, cell migration studies such as the one described in Example 4 herein may be used to determine whether test anti-N-domain antibodies are capable of inhibiting midkine induced cell migration.

In Vivo Assays

In another example, the efficacy of a test anti-N-domain antibody to treat a disease or condition is assessed using an in vivo assay.

For example, a test anti-N-domain antibody may be administered to a non-human mammal (e.g., non-human primate) model of multiple sclerosis or an inflammatory disease such as arthritis.

In another example, the level of an anti-inflammatory cytokine, such as IL-4 is detected in the circulation of a mammal, e.g., using an ELISA. A test antibody that increases the level of the cytokine compared to the level prior to administration and/or in a control mammal to which the test antibody has not been administered is considered suitable for treating the disease or condition.

Midkine-related Disorders

The anti-N-domain antibody antibodies of the present disclosure inhibit MK functions and can therefore be used as therapeutic and preventive drugs for MK-related disease. "MK-related disease" refers to a disease involving MK functions. Examples of such diseases include: diseases attributed to cell growth or angiogenesis, such as cancers (esophageal cancer, thyroid cancer, urinary bladder cancer, colon cancer, stomach cancer, pancreatic cancer, thoracic cancer, liver cancer, lung cancer, breast cancer, neuroblastoma, glioblastoma, uterine cancer, ovarian cancer, pro static cancer, and Wilms tumor) and endometriosis; inflammatory diseases or diseases attributed to cell migration or suppression of regulatory T cell function, such as inflammatory diseases of the kidney, acute renal failure, chronic kidney diseases arthritis, autoimmune disease (organ-specific autoimmune disease, etc.), rheumatic arthritis (rheumatoid arthritis (RA) or osteoarthritis (OA)), multiple sclerosis (relapsing-remitting multiple sclerosis, etc.), inflammatory bowel disease (Crohn disease, etc.), systemic lupus erythematosus (SLE), progressive systematic sclerosis (PSS), Sjogren's syndrome, polymyositis (PM), dermatomyositis (DM), polyarteritis nodosa (PN), thyroid disease (Graves disease, etc.), Guillain-Barre syndrome, primary biliary cirrhosis (PBC), idiopathic thrombocytopenic purpura, autoimmune hemolytic anemia, experimental autoimmune myasthenia gravis (EAMG), amyotrophic lateral sclerosis (ALS), type I diabetes mellitus, transplant rejection, postoperative adhesion, endometriosis, psoriasis, lupus, allergy, asthma, and neutrophil dysfunction; and occlusive vascular diseases or diseases attributed to vascular intimal thickening, such as post-revascularization restenosis, coronary occlusive disease, cerebrovascular occlusive disease, renovascular occlusive disease, peripheral occlusive disease, arteriosclerosis, and cerebral infarction. The MK-related disease is preferably cancer, arteriosclerosis, angiogenesis-related disease, angina pectoris, myocardial infarction, cerebral infarction, cerebral hemorrhage, hypertension, nephritis, chronic obstructive pulmonary disease (COPD) or multiple sclerosis.

The anti N-domain antibody antibodies of the present disclosure inhibit MK functions and can therefore be used for the prevention or inhibition of MK-related disorders such as post-laparotomy adhesions.

Compositions

Suitably, in compositions or methods for administration of the anti-N-domain antibody to a mammal, the antibody is combined with a pharmaceutically acceptable carrier, diluent and/or excipient, as is understood in the art. Accordingly, one example of the present disclosure provides a pharmaceutical composition comprising the anti-N-domain antibody combined with a pharmaceutically acceptable carrier, diluent and/or excipient. In another example, the disclosure provides a kit comprising a pharmaceutically acceptable carrier, diluent and/or excipient suitable for combining or mixing with the antibody prior to administration to the mammal. In this example, the kit may further comprise instructions for use.

In general terms, by "carrier, diluent or excipient" is meant a solid or liquid filler, binder, diluent, encapsulating substance, emulsifier, wetting agent, solvent, suspending agent, coating or lubricant that may be safely administered to any mammal, e.g., a human. Depending upon the particular route of administration, a variety of acceptable carriers, diluents or excipients, known in the art may be used, as for example described in Remington's Pharmaceutical Sciences (Mack Publishing Co. N.J. USA, 1991).

By way of example only, the carriers, diluents or excipients may be selected from a group including sugars (e.g. sucrose, maltose, trehalose, glucose), starches, cellulose and its derivatives, malt, gelatine, talc, calcium sulphate, oils inclusive of vegetable oils, synthetic oils and synthetic mono- or di-glycerides, lower alcohols, polyols, alginic acid, phosphate buffered solutions, lubricants such as sodium or magnesium stearate, isotonic saline and pyrogen-free water. For example, the carrier, diluent or excipient is compatible with, or suitable for, parenteral administration. Parenteral administration includes any route of administration that is not through the alimentary canal. Non-limiting examples of parenteral administration include injection, infusion and the like. By way of example, administration by injection includes intravenous, intra-arterial, intramuscular and subcutaneous injection. Also contemplated is delivery by a depot or slow-release formulation which may be delivered intradermally, intramuscularly and subcutaneously, for example.

Combination Therapies

In one example, the anti-N-domain antibody is administered in combination with another compound useful for treating a disease or condition, e.g., an inflammatory disease, either as combined or additional treatment steps or as additional components of a therapeutic formulation.

For example, the other compound is an anti-inflammatory compound. Alternatively, or additionally, the other compound is an immunosuppressant. Alternatively, or additionally, the other compound is a corticosteroid, such as prednisone and/or prednisolone. Alternatively, or additionally, the other compound is an antimalarial compound, such as hydroxychloroquine or chloroquinine. Alternatively, or additionally, the other compound is methotrexate. Alternatively, or additionally, the other compound is azathioprine. Alternatively, or additionally, the other compound is cyclophosphamide.

Dosages and Timing of Administration

For the prevention or treatment of a disease or condition or relapse thereof, the appropriate dosage of an active agent (i.e anti-N-domain antibody), will depend on the type of disease to be treated, the severity and course of the disease, whether the immunoglobulin is administered for preventive or therapeutic purposes, previous therapy, the patient's clinical history and response to the immunoglobulin, and the discretion of the attending physician. The particular dosage regimen, i.e., dose, timing, and repetition, will depend on the particular individual and that individual's medical history as assessed by a physician. Typically, a clinician will administer an immunoglobulin until a dosage is reached that achieves the desired result.

For in vivo administration of the antibodies described herein, normal dosage amounts may vary from about 10 ng/kg up to about 100 mg/kg of an individual's body weight or more per day. Exemplary dosages and ranges thereof are described herein. For repeated administrations over several days or longer, depending on the severity of the disease or disorder to be treated, the treatment can be sustained until a desired suppression of symptoms is achieved.

In some examples, the antibody is administered at an initial (or loading) dose of between about 1 mg/kg to about 30 mg/kg, such as from about 1 mg/kg to about 10 mg/kg, or about 2 mg/kg or about 3 mg/kg or 4 mg/kg or 5 mg/kg. The antibody can then be administered at a maintenance dose of between about 0.0001 mg/kg to about 1 mg/kg, such as from about 0.0005 mg/kg to about 1 mg/kg, for example, from about 0.001 mg/kg to about 1 mg/kg, such as about 0.005 mg/kg to about 1 mg/kg, for example from about 0.1 mg/kg to about 1 mg/kg, such as about 0.2 mg/kg or 0.3 mg/kg or 0.4 mg/kg or 0.5 mg/kg. The maintenance doses may be administered every 7-30 days, such as, every 10-15 days, for example, every 10 or 11 or 12 or 13 or 14 or 15 days.

Dosages for a particular antibody may be determined empirically in mammals who have been given one or more administrations of the antibody. To assess efficacy of an antibody, a clinical symptom of a disease or condition, e.g., lupus (such as SLE) can be monitored.

Administration of an antibody according to the methods of the present disclosure can be continuous or intermittent, depending, for example, on the recipient's physiological condition, whether the purpose of the administration is therapeutic or prophylactic, and other factors known to skilled practitioners. The administration of an antibody may be essentially continuous over a preselected period of time or may be in a series of spaced doses, e.g., either during or after development of an inflammatory disorder.

Diagnostic Tests

It will be appreciated that the anti-N-domain antibodies described herein may be used as diagnostic agents. For example, the antibodies may be used in diagnostic methods such as ELISAs, radioimmunoassays, immunohistological methods, and western blotting. For example, tissue samples or liquids collected as biopsies from test subjects can be used as specimens for the diagnostic agent of the present invention. The biopsies used are not particularly limited as long as they are targeted by the immunological measurement of MK. Examples thereof can include tissues, blood, urine, serous fluids, spinal fluids, synovial fluids, aqueous humor, lacrimal fluids, saliva or fractionated or processed products thereof. Analysis using the diagnostic agent can be conducted qualitatively, quantitatively, or semi-quantitatively.

The present invention will now be described more specifically with reference to the following non-limiting Examples.

EXAMPLE 1

Preparation of Mouse Anti-human MK Monoclonal Antibodies

MK gene-knockout mice were prepared by a method known in the art (Japanese Patent Laid-Open No. 2002-85058 and Nakamura, E. et al.: Genes Cells 3, p. 811-822).
Preparation of Antigens Human MK mRNAs were prepared from a cultured cell line G-401 derived from Wilms tumor (Tsutsui, J. et al., Biochem. Biophys. Res. Commun. 176, 792-797, 1991). Primers were designed such that they contained a sequence recognized by a restriction enzyme EcoRI (5'-GAATTC-3'). PCR (polymerase chain reaction) of 30 cycles each involving temperature change of 93° C.->37° C.->72° C. was performed using sense PCR primer: 5'-GCGGAATTCAT-GCAGCACCGAGGCTTCCTC-3' (SEQ ID No: 13), and anti-sense PCR primer: 5'-GCGGAATTCCTAGTCCTTTC-CCTTCCCTTT-3' (SEQ ID No: 14) and the human MK mRNAs as templates to prepare human MK cDNAs comprising the MK coding region flanked by EcoRI restriction sites.

The MK cDNAs and expression vectors pHIL301 (containing histidine and a neomycin resistance gene; see Japanese Patent Laid-Open No. 2-104292 and EP Patent No. 0339568) for yeast *Pichia pastoris* GS115 (hereinafter, referred to as "*Pichia* yeast GS115") were digested with a restriction enzyme EcoRI and then ligated using a ligation kit (manufactured by TAKARABIO INC.) to prepare recombinant expression vectors.

The recombinant expression vectors thus prepared were introduced into *Pichia* yeast GS115 (manufactured by Invitrogen Corp.) using electroporation. The vector-introduced *Pichia* yeast GS115 was cultured in a G418-containing medium free from histidine to obtain several clones having the MK gene of interest. The obtained clones were cultured, while induced with methanol. The culture supernatant was collected, and western blotting using rabbit anti-mouse MK polyclonal antibodies was conducted to confirm whether the clones secreted MK.

One of the clones that secreted MK into the culture supernatant by the induction was designated as T3L-50-4P, and this clone was cultured (see Japanese Patent Laid-Open No. 7-39889). The MK secretion products were collected from the culture supernatant and subjected to purification by ion-exchange chromatography and affinity chromatography using a heparin column to obtain highly pure MK.
Immunization The MK-knockout mice were immunized with the antigens. The antigens were prepared as an antigen solution in an amount of 10 µg per mouse diluted with a saline to 0.1 ml, and mixed with 0.1 ml of FCA for emulsification, and this mixture was hypodermically administered to the dorsal regions of the mice. The mice were immunized on a total of 8 occasions, two weeks apart. The 8th immunization was performed by administering a solution containing 10 µg of the antigen solution directly dissolved in 0.1 ml of a saline to the tail veins of the mice through intravenous injection.

On day 6 after the 4th immunization and day 8 after the 6th immunization, sera collected from the eyegrounds of the mice were used to examine serum antibody titers by ELISA.

The ELISA was conducted by the following method: first, the antigen solution was prepared to a concentration of 1.0 µg/ml or 0.1 µg/ml with PBS (pH 7.2 to 7.4) and dispensed in an amount of 50 µl/well or 100 µl/well to a 96-well assay plate (manufactured by BD FALCON, 353912; or manufactured by NUNC, 468667), which was then left standing overnight at 4° C. to immobilize the antigens thereon. The plate was washed three times with 0.05% Tween 20-PBS. Then, 4-fold-diluted BlockAce (manufactured by Dainippon Pharmaceutical Co., Ltd.) in an amount of 100 µl/well or 1% BSA (manufactured by Wako Pure Chemical Industries, Ltd., 019-15134)-0.05% Tween 20-PBS in an amount of 300 µl/well was added thereto, and the plate was left standing at 37° C. for 2 hours or overnight at 4° C. for blocking. The plate was washed three times with 0.05% Tween 20-PBS. Then, an undiluted solution of the culture supernatant in an amount of 50 µl/well or 1 µg/ml purified antibodies in an amount of 100 µl/well was added thereto, and the plate was left standing at 37° C. or room temperature for 1 hour. The plate was washed three times with 0.05% Tween 20-PBS. Then, goat anti-mouse IgG+IgM HRP conjugates (manufactured by BIOSOURCE, AMI3704) diluted 10000-fold with 10-fold-diluted BlockAce (added in an amount of 50 µl/well) or peroxidase-conjugated rabbit anti-mouse IgG (H+L) (manufactured by PIERGE, 31452) diluted 10000-fold with 1% BSA-0.05% Tween-PBS (added in an amount of 100 µl/well) were added thereto as secondary antibodies, and the plate was left standing at 37° C. or room temperature for 1 hour. The plate was washed three times with 0.05% Tween 20-PBS. Then, HRP substrates (25 ml of a substrate solution (10.206 mg/ml citric acid monohydrate and 36.82 mg/ml disodium hydrogen phosphate dodecahydrate in distilled H2O), 10 mg of OPD, and 5 µl of 30% H2O2) in an amount of 50 µl/well or TMB+Substrate Chromogen (manufactured by DAKO, S1599) in an amount of 100 µl/well were added thereto, and the plate was left standing at room temperature for 20 minutes under shading conditions. The reaction was terminated by the addition of 1 N sulfuric acid in an amount of 50 µl/well, and the antibody titers were measured at a wavelength of 492 nm or 450 nm.

Sufficient antibody titers were obtained in ELISA on day 8 after 6 immunizations. Therefore, three days after the additional two immunizations, cell fusion was performed.
Cell Fusion The mice were secured, and their chests were wiped with alcohol-moistened cotton. Blood was collected from the heart using a 2.5 ml syringe and a 23-G needle. After blood collection, the mice were placed in a beaker containing 20 ml of alcohol for disinfection for approximately 3 minutes. The collected blood was placed in a 1.5-ml tube and left at 37° C. for 1 hour and then overnight at 4° C., followed by centrifugation at 3,000 rpm for 10 minutes. The sera were transferred to another 1.5-ml tube and stored at 4° C. after addition of 0.05% sodium azide.

The mice after blood collection were denuded of epithelium using scissors and tweezers. Furthermore, the endothelium was picked up and incised for separation of the spleen. The spleen was washed five times in order with 200 ml of an RPMI1640 S.P medium dispensed in advance to five Petri dishes. The spleen thus washed was placed in a mesh, incised several times with scissors, and crushed using a glass rod. The mesh was washed with an RPMI1640 S.P medium to collect the spleen cells into a 40-ml glass centrifuge. The collected spleen cells were centrifuged at 1200 rpm for 10 minutes, and the supernatant was removed using a suction pipette. 40 ml of an RPMI1640 S.P medium was added to the cells, and the cells were centrifuged at 1200 rpm for 10 minutes. 40 ml of an RPMI1640 S.P medium was added to the obtained spleen cells, and the cells were well stirred. The cell count was measured using a hemocytometer.

Myeloma cells (P3U1) placed in a Petri dish were collected into a 50-ml centrifuge by spraying several times using a pipette. The cells were centrifuged at 1000 rpm for 5 minutes, and the supernatant was removed using a suction pipette. 40 ml of an RPMI1640 S.P medium was added to the cells, and the cells were centrifuged at 1000 rpm for 5 minutes. 40 ml of an RPMI1640 S.P medium was added to the obtained myeloma cells, and the cells were well stirred. The cell count was measured using a hemocytometer.

Based on the results of the cell count measurement, the myeloma cells were placed in the 50-ml glass centrifuge containing the spleen cells such that the ratio between the spleen cells and the myeloma cells was 5:1. After mixing, the cells were centrifuged at 1200 rpm for 10 minutes, and the supernatant was removed using a suction pipette. The centrifuge was then tapped.

After tapping, 1 ml of PEG (polyethylene glycol) was gradually added thereto over 1 minute with stirring and directly mixed for 2 minutes. After PEG mixing, 1 ml of an RPMI1640 S.P medium heated in advance to 37° C. in a water bath was gradually added thereto over 1 minute with stirring. This procedure was repeated three times. Then, 10 ml of an RPMI1640 S.P medium heated in advance to 37° C. was gradually added thereto over 3 minutes with stirring. After medium addition, the mixture was heated at 37° C. for 5 minutes in a 5% CO2 incubator and then centrifuged at 1,000 rpm for 5 minutes, and the supernatant was removed using a suction pipette. The centrifuge was then tapped.

After tapping, (the number of plates for cell inoculation) *10 ml of an RPMI1640 S.P-15% FCS-HAT medium was sprayed thereonto, and the cells were inoculated onto the 96-well plates using an eight-channel micropipette (100 μl each) and a tray designed specifically therefor and using a yellow chip. The cells were cultured at 37° C. for 7 to 14 days in a 5% CO2 incubator. Colony growth was confirmed, and antibody-binding ability was screened by ELISA.

Selection of Anti-MK Positive Antibody-producing Hybridomas 10 days after cell fusion, 12 wells that exhibited significantly high absorbance in ELISA were selected from among the supernatants in the 96-well culture plates and used as samples for cloning. The cell count of the hybridomas was measured, and the hybridoma cells were inoculated to a 96-well culture plate in amounts of 5 cells/well (3 rows), 1 cell/well (3 rows), and 0.5 cells/well (2 rows). Moreover, feeder cells were inoculated to the wells in an amount of 1*10<6> cells/well. On day 5 after cloning, colonies were counted to confirm wells containing one colony. Medium replacement was performed every two to three days. When the colony occupied ⅓ of the well, wells that contained one colony and exhibited a positive reaction were selected using ELISA. Cells obtained from two wells that contained one colony with favorable cell state and were positive in ELISA were used as established cell lines. Antibodies were prepared by an ascites method using the obtained hybridomas and nude mice and purified on a protein G column.

EXAMPLE 2

Characterisation of Mouse Anti-human MK Monoclonal Antibodies

Antibody IP-13 (2.85 mg/ml) was diluted to 5.7 μg/ml in Biacore acetate pH 4.5 buffer and amine coupled to of flow cell (FC) #3 of a CM-4 chip. Approximately 750 units were aimed to be immobilized onto Flow cells (FC) #3 of the CM-4 chip; and FC#1 was blocked using EDC/NHS followed by ethanolamine and was used as reference during the study.

Antibody IP-9 (0.74 mg/ml) was diluted to 7.4 μg/ml in Biacore acetate pH 4.5 buffer and amine coupled to of flow cell (FC) #4 of a CM-4 chip. Approximately 750 units were aimed to be immobilized onto Flow cells (FC) #4 of the CM-4 chip; and FC#1 was blocked using EDC/NHS followed by ethanolamine and was used as reference during the study Preparation of recombinant human midkine (MK17):

Recombinant human midkine was diluted to 15 μM (1 μl of 10 mg/ml in 50 μl of HBS-EP buffer, the calculation was based on molecular weight of 13.4 kDa). Various dilutions of human midkine using HBS-EP buffer were prepared (0, 1, 2, 3, 4, 5, 10 and 20 nM).

Flow cell #1 was used as reference and IP-13 and IP-9 antibody immobilized onto flow cell #3 and #2 respectively; glycine buffer pH2.0 was used to regenerate flow cells between each sample runs. Parameters used during the studies were: injection time=5 min, dissociation time=10 min and flow rate at 40 μl/min. Referencing order: Fc2-Fc1, Fc3-Fc1, Fc4-Fc1.

Antibody IP-10 (2.1 mg/ml) was diluted to 10 μg/ml in Biacore HBS-EP+ buffer and captured on FC#2 to ~300RU for each injection cycle. Recombinant human midkine was midkine was diluted to 746 nM (1 μl of 10 mg/ml in 1 ml of HBS-EP+ buffer, the calculation was based on molecular weight of 13.4 kDa).

Ten separate concentrations ranging from 0-746 nM of human midkine were prepared using HBSEP+buffer.

Flow cell #1 was used as reference and IP-10 antibody captured onto flow cell #2; glycine buffer pH 1.7 was used to regenerate flow cells between each sample run. Two separate assays were run using Single Cycle Kinetics. Parameters used during the studies were: injection time=1 min, dissociation time=10 min and flow rate of 300 min and the following table summarises the kinetics studies using Biacore.

| Antibody | $k_a$ (1/Ms) | $k_d$ (1/s) | $K_A$ (1/M) | $K_D$ (nM) |
|---|---|---|---|---|
| IP-9 | $4.9 \times 10^5$ | $1.2 \times 10^{-4}$ | $4.2 \times 10^9$ | 0.24 |
| IP-13 | $1.4 \times 10^6$ | $2.8 \times 10^{-3}$ | $5.0 \times 10^8$ | 2.02 |
| IP-10 | $1.4 \times 10^7$ | $1.8 \times 10^{-2}$ | $7.8 \times 10^8$ | 1.15 |

IP-9 $K_D = 2.4 \times 10^{-10}$ M
IP-13 $K_D = 2.02 \times 10^{-9}$ M
IP-10 $K_D = 1.15 \times 10^{-9}$ M The heavy and light chains of mAb IP-13 were sequences and the amino acid sequences are shown below (with CDR sequences in bold):

VH (SEQ ID NO: 5):
EVQLQQSGPELVKPGASVKIPCKASGYTFTDYNMGWVKQSHGKSLEWIGD

INPNNGGTIYNQKFKGKATLTVDKSSSTAYMELRSLTSEDTAVYYCARWS

YSNPYFDYWGQGTTLTVSS

VKA (SEQ ID NO: 6):
SIVMTQTPNFLLVSAGDRVTITCKASQSVSNDVSWYQQKPGQSPKLLIY

YASNLYTGVPDRFTGSGYGTDFTFTISTVQAEDLAVYFCQQDYSSPWT

FGGGTKLEIK

EXAMPLE 3

Analysis of Epitopes on Human MK

The midkine N-domain (MK residues 1-61) gene was sequenced and cloned: "WT (1-61)". Mutants of WT (1-61)

MK N-domain were expressed with selected single amino acids mutated from WT to Alanine (A). Anti-N-domain mAbs were then used to detect mutant MK N-domain proteins by Western blot after separation under non-reducing conditions by SDS-PAGE The importance of each residue to the mAb epitope was gauged by intensity of band in the WB using the following key:

No band: canonical residue of epitope

Faint band: minor residue in epitope

Strong band: residue not part of epitope.

Figure 1:
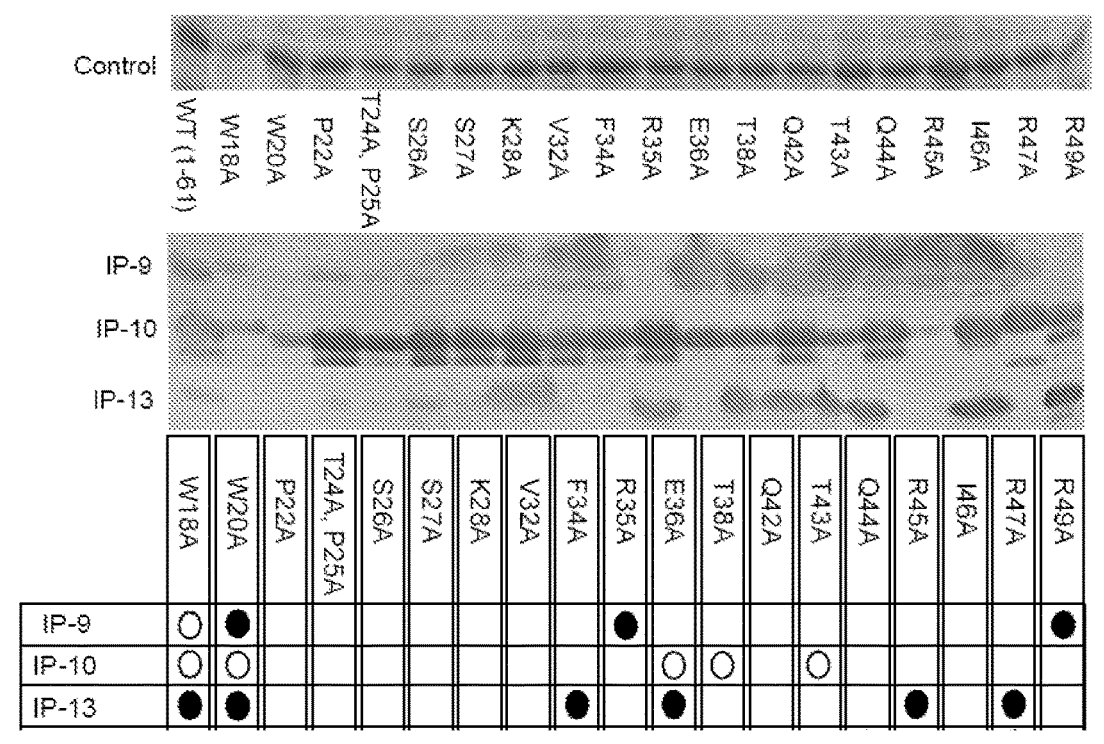

The epitopic residues for each of mAbs IP-9, IP-10 and IP-13 are shown in FIG. 1 and set out below:

Epitope [minor residues in square brackets]

IP-9: [18W], 20W, 35R, 49R

IP-10: [18W], [20W], [36E], [38T], [43T], 45R

IP-13: 18W, 20W, 34F, 36E, 45R, 47R

EXAMPLE 4

Inhibition of MK-Mediated Migration of UMR106 Cells by Anti-MK mAbs

Cell Line

The UMR-106 rat osteosarcoma cell line was originally obtained from the American Type Culture Collection, PO Box 1549, Manassas, Va., USA as a frozen stock (catalog no. CRL-1661; batch no. 58494148).

Cell Culture Media and Reagents

The cells were maintained in: DMEM+Glutamax (DMEM, catalog no. 10569-010 500 mL, lot. no. 778325, Invitrogen/Gibco) supplemented with the following items: Penicillin (10,000 U/mL stock concentration)—Streptomycin (10,000 ug/mL stock concentration) (catalog no. 15140-122 100 mL, lot no. 730849, Invitrogen/Gibco) at a rate of 1 mL/200 mL of DMEM 10% fetal bovine serum (FBS, catalog no. 100099-141, lot no. 6955347Y, Invitrogen/Gibco). The DEM+Glutamax media containing 50 U/mL penicillin, 50 ug/mL streptomycin and 10% FBS is identified as Complete media in this report. The 10% FBS was replaced by 0.3% (w/v) bovine serum albumin (BSA) for the cell migration assays. The BSA was supplied by Sigma-Aldrich, catalog no. A-3192, lot no. 31K1264 and was formulated as a 15% (w/v) stock solution in D-PBS which was sterilized by passage through a 0.22 micron filter and stored at −20° C. prior to use. The cell cultures were maintained in T75 tissue culture-treated flasks in a humidified incubator at approximately 37° C. and 5% carbon dioxide. Cells were sub-cultured twice weekly at a sub-culture ratio ranging from approximately 1:8 to 1:20. Cells were dissociated from the flask by rinsing once with Dulbecco's phosphate buffered saline (DPBS, catalog no. 14190, lot no. 783715, Invitrogen/Gibco) and then incubated with 0.25% Trypsin-EDTA solution (Invitrogen/Gibco) at 37° C. for 2-5 minutes. The cells were then removed by addition of approximately 10 mL of Complete media. The experiments were completed using UMR-106 cells at ~50 to 75% confluency on the day prior to assay. These cultures were washed once with DMEM and cultured overnight in DMEM containing 0.5% FBS. On the day of the experiment the cells were removed from the culture flask by trypsin-EDTA treatment, the trypsin was then quenched by the addition or DMEM+0.5% FBS or DMEM+1% BSA and washed at least once with DMEM+0.3% BSA. The cells were then resuspended in DMEM+0.3% BSA at a final concentration 105 cells per 0.3 mL.

Equipment

The cell migration assays were performed using the following modified Boyden Chamber kits supplied by Millipore Australia: QCM Chemotaxis Cell Migration Assay, 24-well (8 um pores), colormetric (catalog no. ECM 508).

Test and Reference Article Formulation

An aliquot of the 4.69 mg/mL midkine stock solution was thawed at room temperature on the day of the first experiment. On each day of use this stock solution was diluted at the rate of 4.3 uL per 1.0 mL in D-PBS under aseptic conditions at ambient temperature. The resulting 20 ug/mL solution was used immediately for coating the inserts. The unused midkine stock at 4.69 mg/mL was retained at 2-8° C. for use in subsequent experiments.

On the day of the first experiment an aliquot of each of the test compounds was diluted in D-PBS to a final concentration of 2 mg/mL. These working stocks were then be further diluted in DMEM/0.3% BSA to the final concentrations of antibody used in the assays (ranging from 10 to 100 ug/mL). The 2 mg/mL working stocks were retained at 2-8° C. for use in subsequent experiments. The control mouse IgG1 protein was reconstituted in 2.65 mL of sterile water with gentle rotation of the vial until the powder dissolves completely. The resulting 2 mg/mL stock solution was further diluted in DMEM/0.3% BSA to the final concentrations of antibody used in the assays (ranging from 10 to 100 ug/mL). Unused stock solution of the IgG1 protein was aliquoted and stored frozen at approximately −20° C. for the study duration. PBS vehicle control treatments were prepared by dilution of D-PBS at a 1 in 20 (v/v) ratio in DMEM/0.3% BSA.

Study Design

A total of three migration assay experiments were completed. Briefly, the undersides of the transwell filter inserts were pre-coated with midkine protein (20 ug/mL). The inserts were then washed and placed into wells containing control and test treatments and the UMR-106 cells added to the upper chamber of the inserts. The extent of UMR-106 cell migration to the lower face of the insert was assessed after a four hour assay period. Assay readouts were manual counts of the number of cells present on the lower surface.

Cell Migration Assay Method

The cell migration assays were performed using the following modified Boyden Chamber kits supplied by Millipore Australia: QCM Chemotaxis Cell Migration Assay, 24-well (8 um pores), colorimetric (catalog no. ECM 508). This assay method is based on the manufacturers' instructions and the results of the previous method development/validation study at the test facility. QCM Chemotaxis Cell Migration Assay, 24-well (8 um pores)

Protocol

1. Immediately prior to use the midkine protein was diluted to the target concentration of 20 ug/mL in D-PBS (by addition of 4.3 uL of MK17 protein per 1.0 mL of DPBS.
2. The midkine was then immobilized on the underside (outside) face of the membrane of the QCM plate inserts by placing each inserts into wells containing either 0.3 mL of D-PBS or 0.3 mL of D-PBS containing 20 ug/mL of D-PBS. The inserts were then incubated at room temperature for one to two hours.
3. The plate inserts were then rinsed twice with D-PBS by serial transfer into two wells containing approximately 0.5 mL of D-PBS only
4. The plate inserts were then placed into 24-well plates containing 0.5 mL of DMEM+0.3% BSA per well plus or minus control and test treatments. Triplicate wells were used in each treatment.

5. $10^5$ UMR-106 cells, suspended in a volume of 0.3 mL of DMEM+0.3% BSA, were added to the upper (inside) chamber of the QCM plate inserts.
6. The plate was then covered and incubated for 4 hours at 37° C. in a humidified incubator with 5% $CO_2$.
7. The cells/media from the top side of the insert were carefully removed by pippeting out the remaining suspension (in experiments 2-4 the cells around the inside perimeter of the insert were also removed using a low pressure suction pump). The insert was then placed into a clean well containing 400 µL of Cell Stain and incubated for 20 minutes at room temperature.
8. The insert was then rinsed sequentially in three beakers of water.
9. While the insert was still moist, a cotton-tip swab was used to gently remove any non-migratory cells from the interior of the insert. The procedure was then repeated with a second, clean cotton-tipped swab.
10. The insert was allowed to dry.
11. The number of cells on each insert was then estimated by counting the total number of cells in two to four fields at 100× magnification under an inverted microscope (using a Millar's ocular grid to facilitate cell counts)

Data Calculation and Analysis

The mean background OD 560 nm readings obtained for reagent blanks in the absence of cells were subtracted from each test result using Microsoft Excel 2003 spreadsheets (www.microsoft.com). Microsoft Excel 2003 spreadsheets were also used for calculation of group mean and standard deviation values for both readouts. Assay results were represented graphically using GraphPad Prism version 5.01 for Windows, GraphPad Software, San Diego Calif. USA, www.graphpad.com"

Results

The results are shown in FIG. 2. MAbs IP9, IP10 and IP13 inhibited UMR-106 cell migration down to 50.3%, 26.4% and 22.0% respectively.

EXAMPLE 5

EAE Model Animal Test of Mouse Anti-human MK mAbs

Ten week old female C57BL/6 mice (Taconic) were injected subcutaneously in both hind limbs with 100 µlper limb of MOG35-55 peptide (1 mg/ml) emulsified with CFA (2 mg/ml MTB). Immediately following the subcutaneous injection, mice were injected intraperitoneally with pertussis toxin (3.75×, HookeLaboratories), and again 24 hours later. IP-13 (10 mg/kg) was injected intraperitoneally on days 0, 3, 7, 10, 14, 18, 21 and 24. Dextramethasone was injected intraperitoneally every second day. Mice monitored from day 8 to 24 for the parameters described below.

Figure 3:
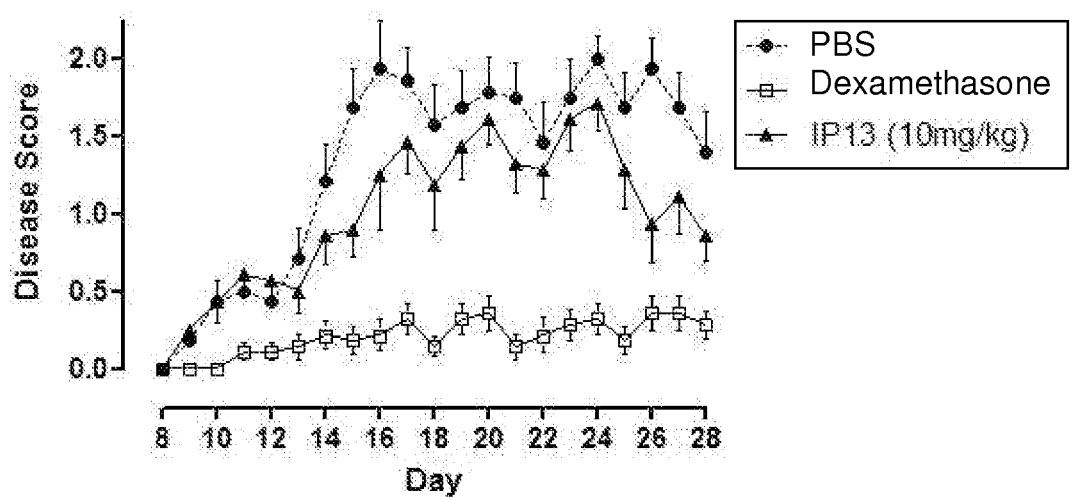
FIG. 3: Scores of EAE model mice to which IP13 has been administered.

Scoring of disease activity observation is described below and results are shown in FIG. 3.

| | |
|---|---|
| 0 | No obvious changes in motor functions of the mouse in comparison to non-immunized mice. |
| 1 | Completely limp tail. |
| 2 | Limp tail and weakness of hind legs |
| 3 | Limp tail and complete paralysis of hind legs. |
| 4 | Complete paralysis. |

Figure 4:
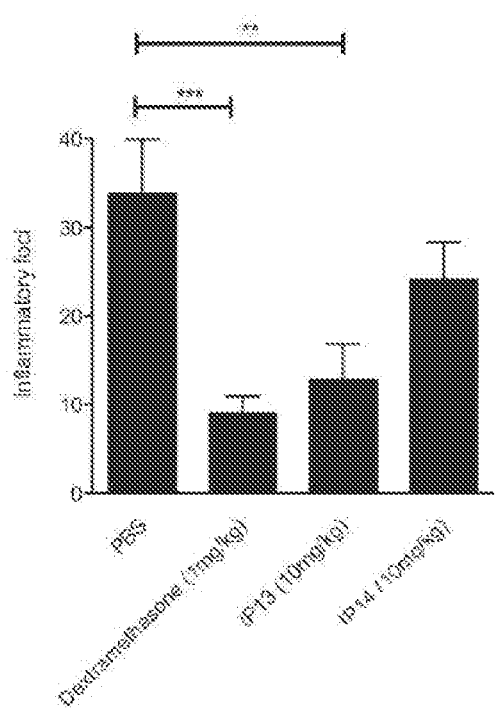
FIG. 4: Inflammatory cell infiltration of spinal cord at day 28.

On day 28 of the study inflammatory cell infiltration of spinal cord was measured. Spinal cords were cut (8 µm thickness), stained with hematoxylin and eosin. Sections were examined by microscope. The number of inflammatory cell foci present in each section were counted and results are shown in FIG. 4.

Figure 5:
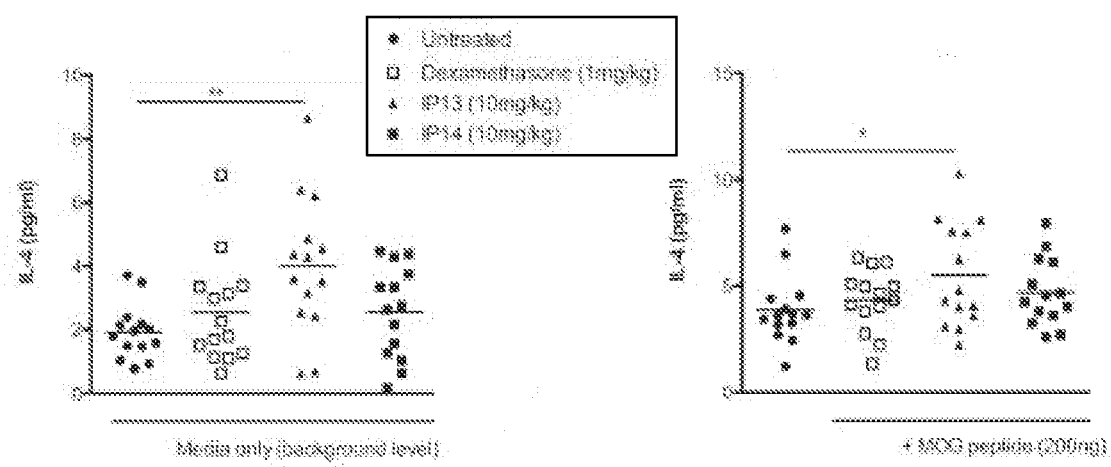
FIG. 5: Anti-inflammatory cytokine IL-4 production by splenic T-cells at day 28.

On day 28 spleens were isolated, cut into 1-3 mm pieces and incubated in media containing collagenase for 45 minutes at 37° C. Following the incubation any remaining pieces were gently mashed through a 75 µm cell strainer and washed thoroughly in IMDM (Invitrogen) followed by MACS buffer. The resulting single cell suspensions were incubated with CD4+ MACS beads and CD4+ T cell were isolated on individual MACS columns following the manufacturers instructions. The flow through CD4-negative cells were treated with Mitomycin C at 50 µg/ml for 30 minutes at 37° C. followed by washing twice in IMDM. CD4+ T cells (2×105 total cells) and Mitomycin C treated CD4− cells (5×106 total cells) were cultured together with 200 ng/ml MOG35-55 peptide for 3 days. Culture supernatant was isolated on day 3 and analyzed with a custom multiplex for the indicated cytokines. Results are shown in FIG. 5.

Figure 6:
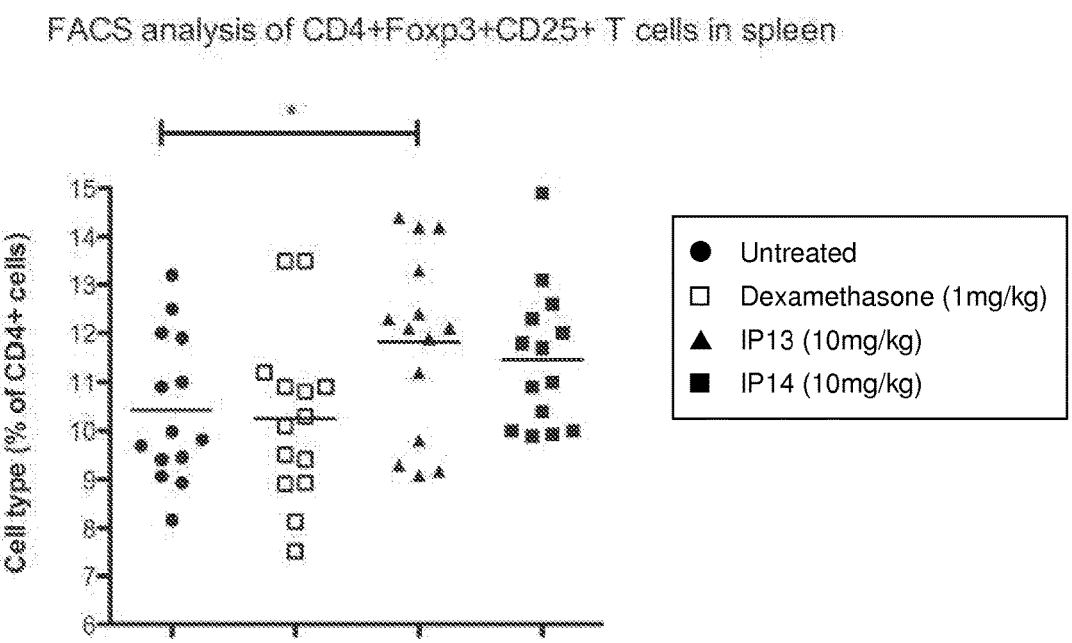
FIG. 6: Anti-inflammatory splenic T reg cells at day 28.

Anti-inflammatory splenic T reg cells were also measured at day 28. CD4+ T cells were cultured as described above. For the assessment of proliferation, cultures were supplemented with 2.5 µCi/ml 3H Thymidine for the final 18 hours of the culture and 3H Thymidine uptake was determined utilizing a TopCount™ Microplate Scintillation Counter. Results are shown in FIG. 6.

EXAMPLE 6

Effect of IP-10 on Kidney Function Following Renal Ischemic Reperfusion Injury Renal ischemia/reperfusion (I/R) is a common cause of acute renal failure (ARF), wherein the renal tubes become susceptible to hypoxic injury. Inflammatory responses to the hypoxia, including renal synthesis of inflammatory cytokines, generation of chemokines and leukocyte infiltration of the kidney, contribute to resultant tissue injury.

Therapies that target specific inflammatory cell types or effector proteins such as chemokines or adhesion molecules, can reduce ischemic ARF in animal models and recover kidney function.

Study Design 10-12 week old male Sprague Dawley rats were assessed for baseline serum blood urea nitrogen (BUN) levels to assess kidney function, with a range of 12-18 mg/dL being the normal BUN range in healthy rats of this age. Kidney damage is evident when BUN levels exceeded 18 mg/dL. Animals were weighed and randomly assigned to either control (saline) or anti-MK mAb (IP10, 10 mg/kg) treatment groups. On Day 0, animals were anesthetized., midline laparotomy was performed and the kidneys exposed. The renal pedicles were clamped to create bilateral acute ischemia. Ischemia was verified by a change in renal color. After approximately 40 minutes, the vascular clamps will be removed and the kidneys reperfused for at least 20 minutes. Within 1 hour after clamp removal the test or control article was administered intravenously (IV) as a bolus (<500 µL) through the tail vein. The abdominal incision was repaired and the animal recovered. On Day 3 test/control articles were once again administered IV as a bolus (<500 µL) through the tail vein.

Figure 7:
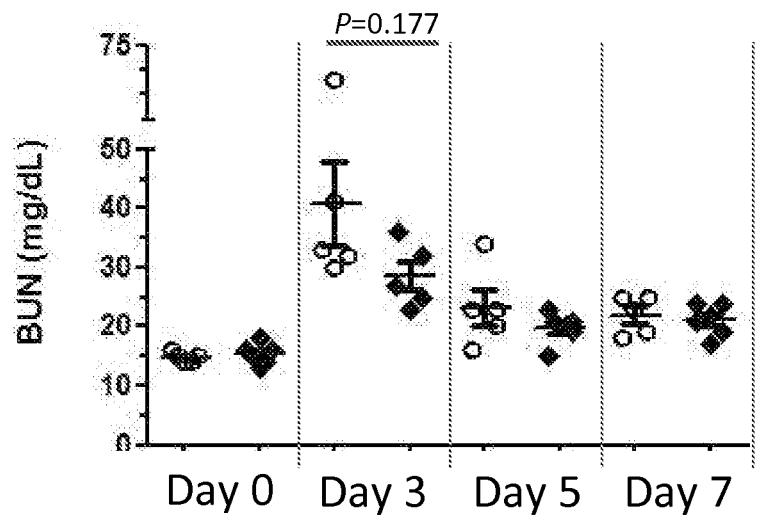
FIG. 7: Effect of IP-10 on kidney blood urea nitrogen (mg/dL) following renal ischemic-reperfusion injury

Animals were observed twice daily for morbidity and mortality. Body weights were also collected on Days 3 and 5 to assess animal health. Serum BUN levels were analyzed on Day 3 (prior to test/control article administration), Day 5 and Day 7. On Day 3, a greater increase in BUN levels (mg/dL) was seen in the control group when compared to the IP-10 treatment group, indicating tissue damage was less severe in the IP-10 treatment group resulting in greater kidney function. Results are shown in FIG. 7.

The invention claimed is:

1. A method for treating a midkine-related disorder comprising administering to a subject in need thereof an isolated or recombinant protein comprising an antigen binding domain of an antibody which specifically binds to an epitope located within the N-domain of midkine (MK) as defined by amino acid residues 1-61 of SEQ ID NO:2, wherein the isolated or recombinant protein comprises
 a heavy chain variable domain comprising heavy chain CDR sequences CDR1, CDR2 and CDR3 as shown in SEQ ID NO:7, SEQ ID NO:8 and SEQ ID NO:9 respectively; and
 a light chain variable domain comprising light chain CDR sequences CDR1, CD2 and CDR3 as shown in SEQ ID NO:10, SEQ ID NO:11 and SEQ ID NO:12 respectively;
 wherein the protein inhibits or reduces a function of midkine, wherein the midkine-related disorder is cancer, inflammation, multiple sclerosis, or post-laparotomy adhesions.

2. A method for treating a midkine-related disorder comprising administering to a subject in need thereof an isolated or recombinant protein comprising an antigen binding domain of an antibody which specifically binds to an epitope located within the N-domain of midkine (MK) as defined by amino acid residues 1-61 of SEQ ID NO:2, wherein the isolated or recombinant protein comprises
 a heavy chain variable domain comprising SEQ ID NO:5 or a sequence exhibiting 95% or greater identity thereto; and
 a light chain variable domain comprising SEQ ID NO:6 or a sequence exhibiting 95% or greater identity thereto, wherein the protein inhibits or reduces a function of midkine, wherein the midkine-related disorder is cancer, inflammation, multiple sclerosis, or post-laparotomy adhesions.

3. The method of claim 1 or 2, wherein the heavy chain variable domain (VH) and the light chain variable domain (VL) are in a single polypeptide chain.

4. The method of claim 3, wherein the isolated or recombinant protein is:
 (i) a single chain Fv fragment (scFv);
 (ii) a dimeric scFv (di-scFv); or
 (iii) at least one of (i) and/or (ii) linked to a Fc or a heavy chain constant domain (CH) 2 and/or CH3.

5. The method of claim 1 or 2, wherein the heavy chain variable domain (VH) and the light chain variable domain (VL) are in separate polypeptide chains.

6. The method of claim 5, wherein the isolated or recombinant protein is:
 (i) a diabody;
 (ii) a triabody;
 (iii) a tetrabody;
 (iv) a Fab;
 (v) a F(ab')2;
 (vi) a Fv;
 (iv) one of (i) to (iii) linked to a Fc or a heavy chain constant domain (CH) 2 and/or CH3; or
 (v) an antibody.

7. The method of claim 1 or 2, wherein the isolated or recombinant protein is a chimeric, de-immunized, humanized or human antibody.

8. The method of claim 1 or 2, wherein the isolated or recombinant protein comprises a human or non-human primate heavy chain immunoglobulin constant region selected from a group consisting of IgG1, IgG2, IgG3, IgG4, IgM, IgE and IgA.

9. The method of claim 1 or 2, wherein the isolated or recombinant protein is conjugated to a compound.

10. The method of claim 1 or 2, wherein the disorder is an autoimmune disease, cancer, an inflammatory disease or multiple sclerosis.

11. The method of claim 1 or 2, wherein the method is for inhibiting post-laparotomy adhesions.

* * * * *